US007456018B2

(12) United States Patent
Gripon et al.

(10) Patent No.: US 7,456,018 B2
(45) Date of Patent: Nov. 25, 2008

(54) HUMAN HEPATOMA LINES, METHODS FOR OBTAINING SAME AND USES THEREOF

(76) Inventors: Philippe Gripon, 15, rue de Chateaudun, F-35000 Rennes (FR); Christiane Guguen-Guillouzo, 41 mail Francois Mitterand, F-35000 Rennes (FR); Christian Trepo, 4, Passage du Verdier Sud, F-69500 Bron (FR); Sylvie Rumin, La Cour, F-35230 Orgeres (FR)

( * ) Notice: Subject to any disclaimer, the term of this patent is extended or adjusted under 35 U.S.C. 154(b) by 0 days.

(21) Appl. No.: 10/482,374

(22) PCT Filed: Jul. 8, 2002

(86) PCT No.: PCT/FR02/02391

§ 371 (c)(1),
(2), (4) Date: Oct. 8, 2004

(87) PCT Pub. No.: WO03/004627

PCT Pub. Date: Jan. 16, 2003

(65) Prior Publication Data
US 2005/0064594 A1 Mar. 24, 2005

(30) Foreign Application Priority Data
Jul. 6, 2001 (FR) ................................. 01 09044

(51) Int. Cl.
C12N 5/08 (2006.01)
C12N 7/00 (2006.01)
C12N 1/10 (2006.01)
(52) U.S. Cl. .................... 435/370; 435/377; 435/258.2; 435/258.3; 435/235.1
(58) Field of Classification Search ................. 435/370, 435/456, 6
See application file for complete search history.

(56) References Cited

U.S. PATENT DOCUMENTS

| 4,393,133 A | 7/1983 | Knowles et al. |
| 5,804,441 A | 9/1998 | Naganori et al. |

FOREIGN PATENT DOCUMENTS

| EP | 0972828 | * | 1/2000 |
| EP | 0972828 A1 | | 1/2000 |
| WO | WO94/08598 | | 4/1994 |
| WO | WO96/30492 | | 10/1996 |

OTHER PUBLICATIONS

Chiu et al., "The Formation of Bile Canaliculi in Human Hepatoma Cell Lines," 11(5) Hepataology 834-842 (May 1990).*
Encke et al., "Genetic Immunization Generates Cellular and Humoral Immune Responses Against the Nonstructural Proteins of the Hepatitis C Virus in a Murine Model," J Immunol. 161(9):4917-23, 1998.*
Fipaldini et al., "Expression of Hepatitis C Virus cDNA in Human Hepatoma Cell Line Mediated by a Hybrid Baculovirus-HCV vector," Virology 255, 302-311 (1999).*
Houghton et al. "Prospects for a vaccine against the hepatitis C virus," Nature, vol. 436, Aug. 18, 2005.*
Hsieh et al., "Improved Gene Expression by a Modified Bicistrionic Retroviral Vector," Biochemical and Biophysical Research Communications, vol. 214, No. 3 (1995).*
Karnasuta et al., "Complete Development of the liver stage of Plasmodium falciparum in a human hepatoma cell line," Am J Trop Med Hyg, 53(6): 607-11, (Dec. 1995).*
Liu et al. "Expression of precore and core proteins of hepatitis B virus in human hepatoma cell line," Di Yi Jun Yi Da Xue Xue Bao, 22(2): 174-6 (2002).*
Nozaki et al., "Establishment of a human hepatoma cell line, HLE/2E1, Suitable for Detection of P450 2E1-Related Cytotoxicity," In. Vitro. Cell. Dev. Biol.-Animal 36:566-570, Oct. 2000.*
Roberts et al., "Characterization of the Ah receptor mediating aryl hydrocarbon hydroxylase induction in the human liver cell line Hep G2," Arch Biochem Biophys. 276(2):442-50 1990.*
Rodriquez-Antona et al., "Chrome P450 expression in human hepatocytes and hepatoma cell lines: molecular mechanisms that determine lower expression in cultured cells," Xenobiotica 32(6): 505-20 (2002).*
Saito et al., "Effect of Dexamethasone, dimehtylsulfoxide and sodium butyrate on a human hepatoma cell line PLC/PRF/5," Cancer Biochem. Biophys., vol. 13, pp. 75-84 (1992).*
Speiss et al., "Sequence of Human Asialoglycoprotein Receptor cDNA," Journal of Biological Chemistry 260 (4) pp. 1979-1982 (1985).*
Sugimoto et al., "Expression of Functional CD40 in Human Hepatocellular Carcinoma," Hepatology, 30(4) pp. 920-926 (1999).*
Sumida et al., "Quantitative Analysis of Constitutive and Inducible CYPs mRNA Expression in the HepG2 Cell Line Using Reverse Transcription-Competitive PCR," Biochemical and Biophysical Research Communications 267, 756-760 (2000).*
Wang et al. ("In situ and in vitro photoaffinity labeling of the nuclear aryl hydrocarbon receptor from transformed rodent and human cell lines," Arch Biochem Biophys 287(1): 186-94 (1991).*
Wang et al., "Lipid and lipoprotein metabolism in Hep G2 cells," Biochim Biophys Acta 961 (3): 351-63; Aug. 12, 1988.*
Zeiger et al., "Inducing Effects of Dioxin-like Polychlorinated Biphenyls on CYP1A in the Human Hepatoblastoma Cell Line HepG2, the Rat Hepatoma Cell Line H4IIE, and Rat Primary Hepatocytes: Comparison of . . . ," Toxicological Sciences, 63, 65-73 (2001).*
Zhou et al., "Glutathione S-transferase expression in hepatitis B virus-associated human hepatocellular carcinogenesis," Cancer Res., 57 (13): 2749-53, Jul. 1997.*

(Continued)

Primary Examiner—Mary E Mosher
(74) Attorney, Agent, or Firm—Buchanan Ingersoll & Rooney PC

(57) ABSTRACT

Human hepatoma cell lines are provided that comprises a set of cells clonally derived from a cancerous human liver cell, in which each cell of the set expresses a receptor having an affinity for binding a virus of the *Flaviviridae* genus and a virus of the *Hepadnaviridae* genus to enable infection by viruses of both genus in native forms, and in which each cell of the set exhibits susceptibility to infection by a hepatotropic parasite of the *Leishmania* genus in a native form. Various compositions and methods relating to diagnostic, therapeutic, and prophylactic embodiments are also provided.

6 Claims, 13 Drawing Sheets

OTHER PUBLICATIONS

Bchini et al., "In Vitro Infection of Human Hepatoma (HepG2) Cells with Hepatitis B Virus," Journal of Virology, vol. 64, No. 6, p. 3025-3032 (1990).*

Garson et al., "Suramin Blocks Hepatitis C Binding to Human Hepatoma Cells In Vitro," Journal of Medical Virology, 57, pp. 238-242 (1999).*

LeSeyec et al., "Infection Proces of the Hepatitis B Virus Depends on the Presence of a Defined Sequence in the Pre-S1 Domain," Journal of Virology, vol. 73, No. 3, pp. 2052-2057 (1999).*

El Hag et al., "Liver morphology and function in visceral leishmaniasis (Kala-azar)," J. Clin. Pathol, 47: pp. 547-551 (1994).*

Nomura et al., "Human hepatitis B virus X protein is detectable in nuclei of transfected cells, and is active for transactivation," Biochimica et Biophysica Acta 1453, pp. 330-340 (1999).*

Saeed et al., "Serum erythropoietin concentration in anaemia of visceral leishmaniasis (kala-azar) before and during antimonial therapy," British Journal of Haematology, 100, pp. 720-724 (1998).*

McCoy et al., "N-Formylpeptide and Complement C5a Receptors Are Expressed in Liver Cells and Mediate Hepatic Acute Phase Gene Regulation,". Exp Med, vol. 182, pp. 207-217 (1995).*

Muller et al., "Thrombospondin related anonymous protein (TRAP) of Plasmodium falciparum binds specifically to sulfated glycoconjugates and to HepG2 hepatoma cells suggesting a role for this molecule in sporozoite invasion of hepatocytes," The EMBO Journal, vol. 12, No. 7, pp. 2881-2889 (1993).*

XM Wang et al., "Effects of 5-Azacytidine and Butyrate on Differentiation and Apoptosis of Hepatic Cancer Cell Lines," Annals of Surgery, vol. 227, No. 6, pp. 922-921 (1998).*

Marianneau et al., "Differing Infection Patterns of Dengue and Yellow Fever Viruses in a Human Hepatoma Cell Line," The Journal of Infectious Diseases, 178, pp. 1270-1278 (1998).*

S.R. Wang et al (Biochimica et Biophysica Acta 961:351-363, 1998).*

Chiu et al (Hepatology 11(5):834-842, May 1990).*

Nomura et al (Biochimica et Biophysica Acta 1453:330-340, 1999).*

Le Seyec et al (Journal of Virology 73:2052-2057, 1999).*

Germi et al (Journal of Medical Virology 64:6-12, 2001).*

Hollingdale et al (Journal of Immunology 132:909-913, 1984).*

Saito et al (Cancer Biochemistry Biophysics 13:75-84, 1992).*

Karnasuta et al (American Journal of Tropical Medicine and Hygiene 53: 607-11, 1995).*

Gripon, Philippe et al., "*Regulation by Dimethylsulfoxide, Insulin, and Corticosteroids of Hepatitis B Virus Replication in a Transfected Human Hepatoma Cell Line,*" 28(3) Journal of Medical Virology 193-199 (Feb. 1989).

Lian, Wei-Nan et al., "*Targeting of Aminopeptidase N to Bile Canaliculi Correlates With Secretory Activities of the Developing Canalicular Domain*" 30(3) Hepatology 748-760 (Sep. 1999).

Chiu, Jen-Hwey et al., "*The Formation of Bile Canaliculi in Human Hepatoma Cell Lines,*" 11(5) Hepatology 834-842 (May 1990).

Neurath, A. Robert et al., "*Search for Hepatitis B Virus Cell Receptors Reveals Binding Sites for Interleukin 6 on the Virus Envelope Protein,*" 175 J. Exp. Med. 461-469 (Feb. 1992).

Saito, Hidetsugu et al., "*Effect of Dexamethasone, Dimethylsulfoxide and Sodium Butyrate on a Human Hepatoma Cell Line PLC/PRF/5,*" 13 Cancer Biochemistry Biophysics 75-84 (Nov. 1992).

Zvibel, Isabel et al., "*Phenotypic characterization of rat hepatoma cell lines and lineage-specific regulation of gene expression by differentiation agents,*" 63 Differentiation 215-223 (1998).

* cited by examiner

COUPE SCHEMATIQUE DU FOIE

GROWTH MODIFICATION
A croissance
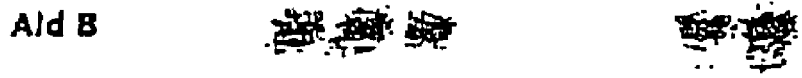
Alb
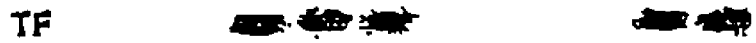
Ald B
TF
Cyp 2E1
Cyp 3A
GROWTH MODIFICATION
B croissance
Alb
Ald B
Cyp 3A
FIGURE 9

A
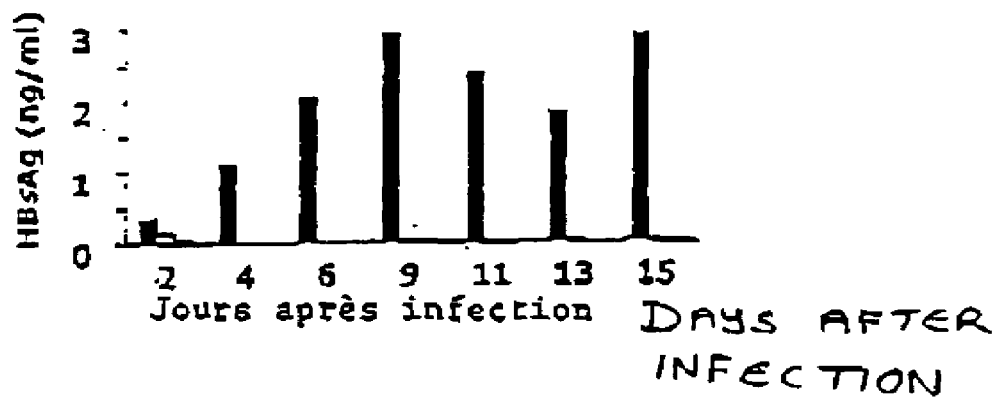
B
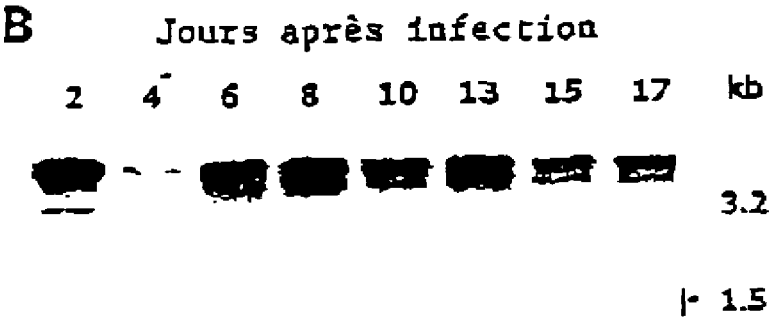
C
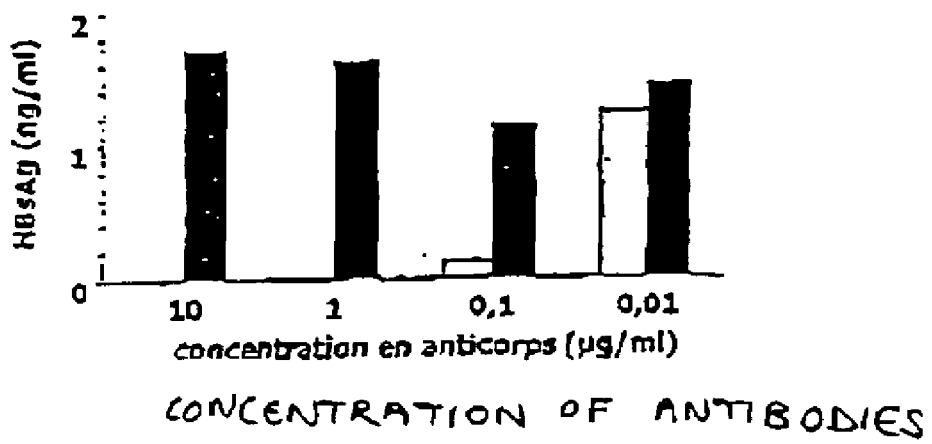
FIGURE 11

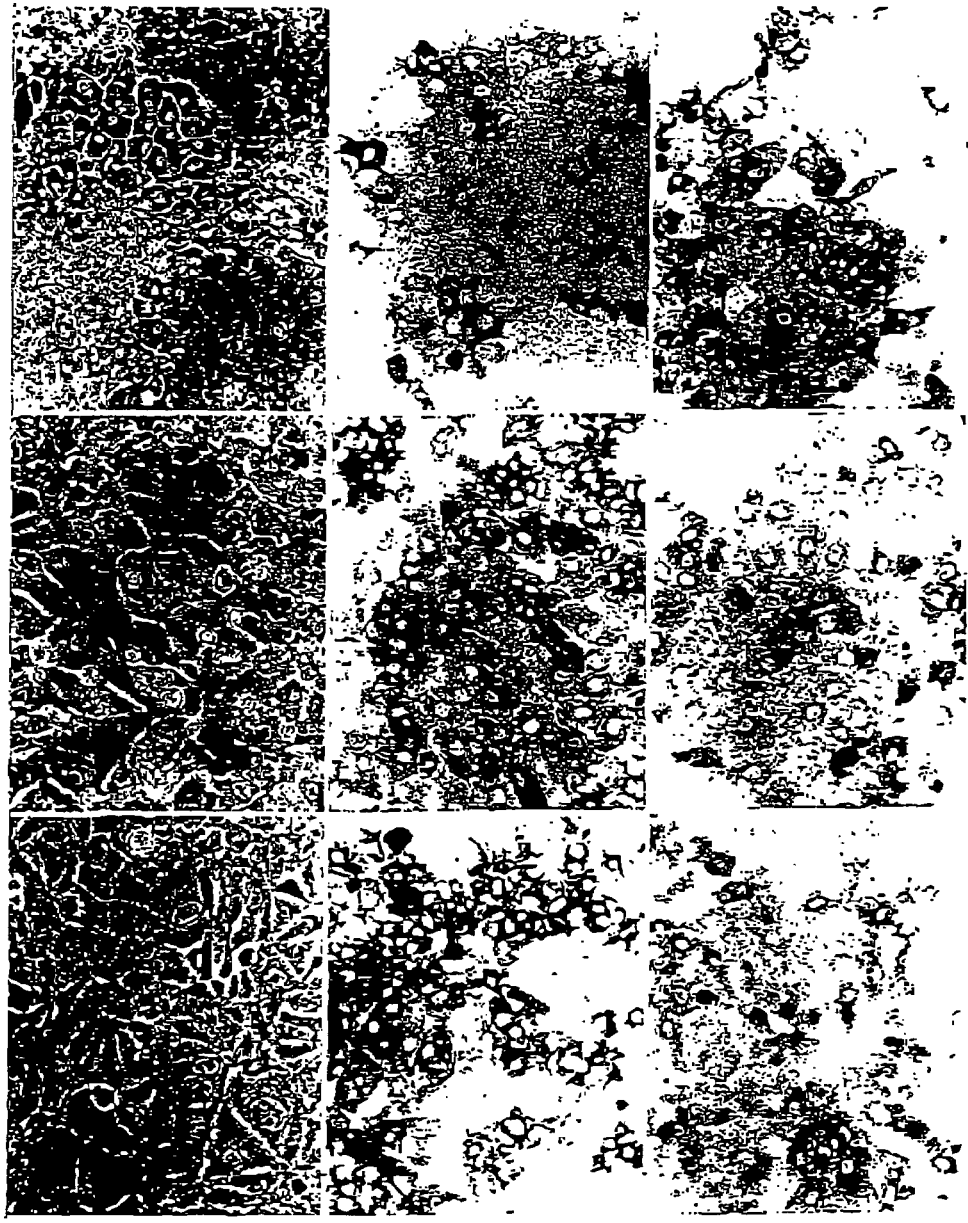

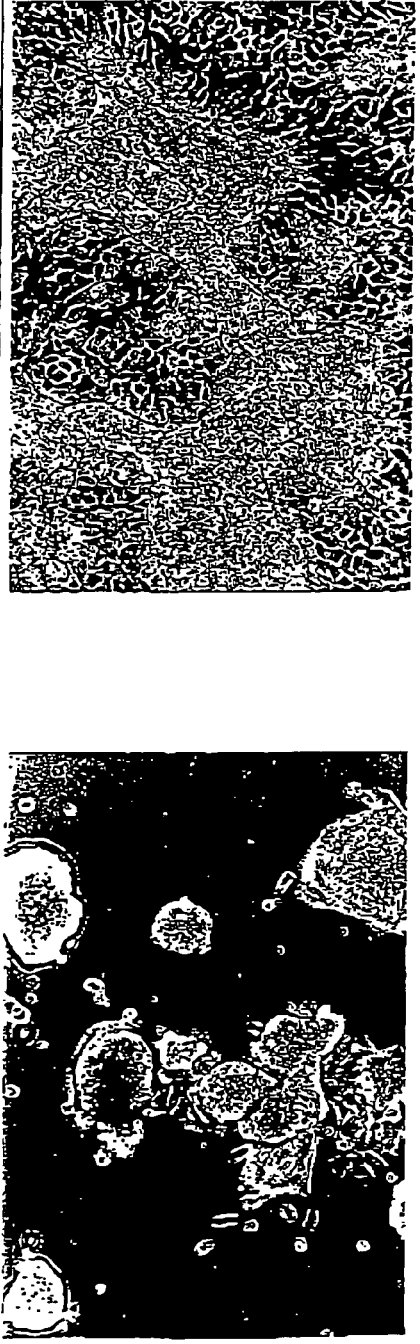
Figure 13A
Figure 13B

HUMAN HEPATOMA LINES, METHODS FOR OBTAINING SAME AND USES THEREOF

CROSS REFERENCE TO RELATED APPLICATIONS

This application is a national phase of PCT/FR02/002391 filed Jul. 8, 2002, which claims priority of the French Application No. 01/09044, filed on Jul. 6, 2001, which are hereby incorporated by reference in their entireties and are relied upon.

The invention relates to novel human hepatoma lines. It also relates to methods for obtaining same and their uses in diagnostic, therapeutic and prophylactic applications.

INCORPORATION-BY-REFERENCE & TEXTS

The material on the accompanying compact disc is hereby incorporated by reference into this application. The accompanying compact disc contains one file, ALX1 GENERAL-#1308566-v1-03247515 TXT.TXT created on Feb. 13, 2008, is 1.2 KB. The file can be accessed using Microsoft Word on a computer that uses Windows OS.

Hepatitis B is an infectious disease which is widespread throughout the world. Its virus (abbreviated to HBV) is a small virus with DNA possessing a high host specificity. In fact, only humans and the higher primates are infected by this virus, which strongly limits the in vivo study models of this infection. However, a "duck" model exists which allows the study of an entire replication cycle of a hepadnavirus (in vitro and in vivo). This hepadnavirus, although close to the HBV virus, however has a somewhat different biology. Moreover, the metabolic behaviour of the duck cannot be simply compared to that of humans.

HBV moreover shows a strong tropism for the liver and preferentially targets the parenchymatous cells. Also, unlike other viruses, only the differentiated hepatic cells can be infected.

A cell line derived from hepatomas has allowed rapid progress in the understanding of the replication mechanisms. This line, which is widely used, is referenced under the name HepG2. A derived clone HepG2 2.2.15 has the advantage of possessing a considerable ability to proliferate and actively replicate the virus. However, this replication is possible only after the introduction of the viral DNA into the cells, by transfection. Natural infection of this line by the HBV has proved impossible. Moreover, due to the age of this line, the karyotype of its cells is broadly modified, which makes it an imperfect model for mimicking human hepatocytes. Finally, the differentiation capacity of these cells remains fairly limited.

Other more or less differentiated cell lines have been proposed. In particular the line Hep3B, which is slightly different from the line HepG2, and which has the same limits as the latter can be mentioned. All the line infection tests have proved negative or disappointing in terms of effectiveness.

In order to study the mechanisms of HBV infection, a model of human hepatocytes in primary culture has been developed. This model is very useful in involving human hepatocytes and allowing access to the whole viral cycle. However, it is difficult and tedious to manipulate, and obtaining bioptic fragments is increasingly difficult and random.

The inventors' work in this field has led them to record that human hepatoma lines, actively multiplying whilst being capable of being infected by parasites and/or viruses, in particular HBV, could be obtained by carrying out a cell selection under specific conditions.

The invention therefore aims to provide new human hepatoma lines capable of being infected by parasites and/or viruses, and the cells or elements of these cells originating from these lines.

It also relates to a process for selecting such lines.

A subject of the invention is also the uses of these lines in diagnostic, therapeutic and prophylactic applications.

According to the present invention, the human hepatoma cell lines are characterized in that they are capable of being infected naturally by parasites and/or viruses; said parasites may or may not be hepatotropic, such as *Plasmodium* or parasites of the genus *leishmania*; and express receptors of the family of the *Flaviviridae* and *Hepadnaviridae* viruses, preferably HBV and HCV.

These new lines thus allow complete study of the cycle of the parasites and/or viruses in particular the viral cycle of the HBV, from the natural infection stage to the replication and/or propagation of the virus. It will be observed in this respect that no human hepatoma cell line is at present capable of being infected by *Plasmodium falciparum*, i.e. that no human hepatoma cell line is capable of supporting the development of mature forms of this hepatotropic parasite (schizonts). Moreover, due to its ability to proliferate, these lines are very easy to manipulate.

According to another aspect of the invention, these lines are capable of reaching an advanced level of differentiation.

In particular, the cells resulting from the lines according to the invention make it possible to reach a stage of hepatic differentiation, i.e. a morphology close to cells constituting the liver, such as the hepatocytes and/or the biliary cells with in particular:
 the formation of trabeculae of parenchymatous cells,
 the formation of functional biliary canaliculi, with at cell level, the reconstitution of a biliary pole.

Throughout the Application, reference is made to typical notions of the structural organization of the liver cells. These notions, in particular the biliary pole, are explained in the preamble to the "Results" paragraph of Example 1 hereafter. It is surprising to note that the cells originating from the lines according to the invention are capable of practically identically mimicking the structural organization of the liver cells and of reproducing its functions: in fact, the biliary canaliculi formed by the cells of the lines according to the invention are functional, i.e. capable of playing their detoxification role. This functional differentiation is moreover highly advanced: the cells of the human hepatoma cell lines according to the invention can express the functions characteristic of the hepatocyte, namely:
 the production of plasmatic proteins, in particular albumin, and transferrin,
 the detoxification function, in particular:
  the expression of various forms of P450 cytochromes, such as CYP2E1, CYP3A and/or CYP1A, the expression of various forms of detoxification phase II enzymes in particular GSTα,
  the conjugation of biliary salts,
  the elimination of urea.
 the energy regulation function:
  the storage of sugar in the form of glycogen and the production of glucose by glycolysis, in particular, the expression of aldolase B, and/or neoglucogenesis,
  metabolism of lipids.

It will be noted with interest that no human hepatoma cell line was capable of producing cells which could reach a level of differentiation such that these cells could express practically all of the functions of the normal human hepatocyte, in particular, the detoxification functions of phases I and II (CYP2E1, CYP3A, CYP1A and GSTa).

According to an unexpected aspect, the cells originating from the lines according to the invention possess properties of pluripotent cells, in particular properties of resident and/or oval stem cells, i.e. capable of differentiating towards the hepatocyte, biliary, pancreatic and/or intestinal route.

The resident stem cells are liver cells, capable, during a massive destruction of the liver, of actively multiplying in order to regenerate the part destroyed. These cells can evolve towards a hepatocyte or biliary lineage (FIG. 1). Moreover, these resident stem cells, sometimes also designated oval cells, have the ability to differentiate into different cell types such as pancreatic, intestinal and/or hepatic cells.

Another advantage of the lines according to the invention lies in their ability to proliferate actively. Thus, in the proliferation phase, the cell population doubles in approximately 24 hours.

The invention relates in particular to the cell line filed on 5th Apr. 2001 at the Collection Nationale de Cultures de Microorganismes, Institut Pasteur, 25 rue du Docteur Roux, F-75724 Paris Cedex 15, under No. I-2652.

This line, called HepaRG, is an example of a cell line having all the characteristics of the lines according to the invention at the same time: it can be infected naturally by parasites, viruses, it has the morphological characteristics set forth above, and possesses all the biological functions of a hepatic cell. It appears to be a virtually perfect model of the hepatic cells.

Also included within the scope of the invention are cells or elements of cells originating from the lines according to the invention and in particular, membranes, receptors and/or antigens originating from this membrane, cytoplasm, nucleus, genes and/or gene products, DNA, mRNA, cDNA, proteins, peptides.

Moreover, the invention aims to provide methods for obtaining and selecting such lines.

This involves in particular a process for selecting human hepatoma cell lines comprising:
a phase of cell proliferation in a culture medium comprising continuously at least one cortico-steroid at a non-toxic concentration which promotes the differentiation of normal human hepatocytes, and in particular their optimum differentiation.
then, having reached confluence, a phase of cell differentiation in this same medium, by the addition of DMSO, in a quantity sufficient to induce differentiation,
this process being repeated several times, preferentially 3 times, if desired.

This cell selection process is indispensable for maintaining the properties of the lines according to the invention. In fact, this selection process induces high cell mortality. Example 3 below demonstrates the necessary cooperation between the cortico-steroid and the DMSO.

The phrase "non-toxic concentration which promotes the differentiation of normal human hepatocytes", is used to refer to the cortico-steroid concentration promoting, during its addition to a culture of normal human hepatocytes, the differentiation of the cells towards a morphology and a functional state described in the preamble to the "Results" paragraph of Example 1. This concentration is non-toxic, i.e. its addition does not lead to a cell mortality rate greater than approximately 10%.

Moreover, the term "quantity sufficient to induce the differentiation" is used to refer to the quantity of DMSO necessary to induce the differentiation of a culture of normal human hepatocytes.

It will be noted with interest that a preferential process comprises a cortico-steroid present at a high concentration, continuously in the medium, in contrast to the processes usually used in hepatoma culture. Surprisingly, the presence of this cortico-steroid in no way prevents the lines from proliferating.

This selection process has made it possible to develop a process for obtaining the lines according to the invention comprising a stage of biopsy of a solid tumor of hepatocarcinoma type, a stage of isolation of the cell population using a proteolytic enzyme and a stage of selection of the lines using the selection process detailed above.

The proteolytic enzyme preferentially used is trypsin and/or collagenase.

The invention also proposes a process for infecting hepatic cells with a hepatotropic parasite and/or a virus comprising:
a selection phase using the abovementioned selection process,
a differentiation phase allowing the cells to reach a morphology close to the hepatocyte using culture medium comprising at least one cortico-steroid at a non-toxic concentration which promotes optimum differentiation of normal human hepatocytes, with DMSO added to it, in a quantity sufficient to induce differentiation,
an infection phase with incubation of the hepatic cells in a culture medium comprising at least one cortico-steroid at a non-toxic concentration which promotes optimum differentiation of normal human hepatocytes, to which the infectious source is added.

The hepatotropic parasite can be a *Plasmodium* and the virus, HBV or HCV.

A possible infectious source is the supernatant of HepG2 cells and/or a patient's serum.

The culture media used for the selection, obtaining and infection processes preferably contain insulin in a quantity sufficient to promote the survival of normal human hepatocytes, preferentially from 2.5 µg/ml to 10 µg/ml, in particular of the order of 5 µg/ml.

The insulin makes it possible to considerably improve the viability of the cells.

Moreover, the cortico-steroids of these culture media are preferably hydrocortisone hemisuccinate and dexamethasone. Other inducers of differentiation can be used, in particular retinoic acid and/or its synthetic analogues, oestrogens and thyroid hormones.

The term "synthetic analogues" is used to refer to the analogues of said cortico-steroids and retinoids of non-natural origin.

The corticoid concentration is from $10^{-7}$ M to $10^{-4}$ M, preferentially approximately $5.10^{-5}$ M for the hydrocortisone hemisuccinate and approximately $10^{-5}$ M for the dexamethasone. Finally, the DMSO concentration, when the latter is added to the culture media, is from 1% to 4%, preferentially approximately 2%.

The invention also relates to a process for transfection of the lines according to the invention using a vector comprising the complete sequence and/or part of genetic material from the HBV and/or HCV viruses. It also relates to a high-flow-rate screening process of differentially expressed genes using a chip-type tool produced from the lines and/or cells and/or parts of cells according to the invention, preferably, these genes being differentially expressed under the effect of culture conditions, exposure to a molecule and/or virus and/or a parasite.

An example of a chip-type tool is given in Example 7 hereafter. It is a cDNA chip the construction of which allows high-flow-rate screening of differentially expressed genes.

The invention finally covers the use of the different culture media allowing the obtaining, maintaining, proliferation, selection, differentiation, transfection, infection of the lines according to the invention. It involves in particular the use of a culture medium comprising continuously at least one cortico-steroid, preferentially hydrocortisone hemisuccinate at a non-toxic concentration which promotes optimum differentiation of normal human hepatocytes, in order to maintain the stability of the cell population lines and/or of the cells according to the invention; as well as the use of a culture medium continuously comprising at least one cortico-steroid, preferentially hydrocortisone hemisuccinate at a non-toxic concentration which promotes optimum differentiation of normal human hepatocytes, with DMSO added in a quantity sufficient to induce differentiation of the cells originating from the lines according to the invention; and use of the culture medium continuously comprising at least one cortico-steroid at the above-mentioned concentration as well as sodium butyrate at a concentration sufficient to induce a biliary-type differentiation, preferably a concentration of 2.5 to 5 mM, in particular approximately 3.75 nM.

As already indicated, the lines according to the invention are capable of evolving towards distinct differentiation routes. The differentiation route is strongly influenced by the choice of culture medium. Evolution towards the hepatic, biliary and pancreatic routes are illustrated by Example 4.

Human hepatoma lines according to the invention are the subject of a numerous applications, given their high differentiation capacity, their considerable functionality and their ease of manipulation.

A first useful application corresponds to the use of the lines and/or cells originating from the lines according to the invention, for metabolic and/or toxicity tests intended for the evaluation of new medicaments and/or nutritional constituents and/or environmental pollutants.

In fact, the lines according to the invention are at present the best model mimicking normal human hepatocytes, in particular in terms of detoxification.

In particular the lines according to the invention allow the manufacture of an extracorporeal bioreactor for the transient treatment of acute hepatocellular insufficiencies. The invention also covers the use of the lines according to the invention for the screening and/or manufacture of new vaccines and/or antiviral molecules, in particular for the screening of molecules active vis-à-vis one of the viral cycle stages; for the manufacture of antibodies directed against a virus belonging to the *Flaviviridae* and *Hepadnaviridae* family, in particular directed against the HBV and HCV and/or their cell membrane receptors; for carrying out viral neutralization and/or vaccinal composition tests comprising at least viral particles and/or polypeptides obtained after infection and/or transfection of the lines according to the invention, combined with a pharmaceutically acceptable vehicle and/or excipient and/or adjuvant.

The lines according to the invention are advantageously used for the purposes of validating the virucidal capacity of disinfectant chemical products.

The invention also proposes a new method for evaluating the virucidal capacity of a disinfectant chemical product for cleaning equipment, premises and/or surfaces comprising:
  bringing the viruses into contact with said equipment, premises and/or surfaces,
  the disinfecting of said equipment, premises and/or surfaces with said disinfectant chemical product,
  then the contamination of cells according to the invention, by the viruses having survived the disinfecting.

Other characteristics and advantages of the invention are given in the examples which follow. They relate, for illustration purposes, to the line I-2652 deposited at the CNCM, called HepaRG.

BRIEF DESCRIPTION OF THE DRAWINGS

FIGS. 12 and 13, biliary and pancreatic differentiations,

EXAMPLE 1

Isolation of Hepatoma Cell Line

1. Materials and Methods

Cells were isolated from a liver tumor taken from a patient suffering from a hepatocarcinoma and viral hepatitis C. The whole procedure was carried out in accordance with French law and regulations and approved by the Comite National d'Ethique, and confidentially.

The samples were cut into fine sheets, then rinsed with a HEPES-based buffer solution [(pH 7.7; 140 mM NaCl, 2.68 mM KCl, 0.2 mM $Na_3HPO_4$ and 10 mM HEPES], and digested with 0.025% of collagenase D (Boehringer Mannheim) diluted in the same buffer solution with 0.075% of $CaCl_2$ added (addition under gentle stirring at 37° C.). After two washings with the HEPES buffer solution, the cells are resuspended in a Williams' medium E, supplemented with 10% of foetal calf serum (FCS), 100 U/ml of penicillin, 100 μg/ml of streptomycin, 5 μg/ml of insulin, 2 mM/ml of L-glutamine and $5.10^{-7}$ M of hydrocortisone hemisuccinate. The cell suspension is then distributed into different wells on a plastic support. After several weeks, the cell growth is sufficient to produce a culture. Its population is heterogenous, but the cells are highly differentiated and have a hepatocyte-type morphology. The wells having the most homogenous cell populations are separated with trypsin, then redistributed.

After 3 passages, the cells are aliquoted, then frozen in the culture medium with 10% of DMSO added, and preserved in liquid nitrogen. After thawing, the well having the greatest proportion of cells having a hepatocyte-type morphology is selected. The cells are cultured in the culture media used for their isolation and/or in the differentiation medium used to complete the cell selection.

In order to obtain a more frequent hepatocyte differentiation in the line, the HepaRG cells originating from the first selection are cultured in a Williams' medium E, with 5 µg/ml of insulin, 100 U/ml of penicillin, 100 µg/ml of streptomycin, $5.10^{-7}$ M of hydrocortisone hemisuccinate, 2 mM/ml of L-glutamine and 10% of FCS added.

The cells are subjected to a passage every 10-15 days, at a 1/5 dilution. The differentiation phase takes place in two stages:
  the cells are maintained in their growth medium for two weeks, confluence being reached at the end of one week,
  they are then maintained in a differentiation medium (corresponding to the preceding culture medium, with 2% of DMSO added) for another two weeks, the medium being replenished every 2 or 3 days.

Cytogenetic Analysis

The karyotype of the HepaRG cells was analyzed after 8 passages. The cells were first maintained for 24 to 48 hours in RPMI 1640 with 10% of FCS added, then blocked in metaphase by exposure to Colcemide (10 µg/mL) for 45 minutes.

The cells were then treated with a hypotonic solution (0.1 M of $MgCl_2$), fixed with Carnoy's acetic solution and the chromosomes revealed by RHG staining.

2. Results

Preamble

Figure 2:
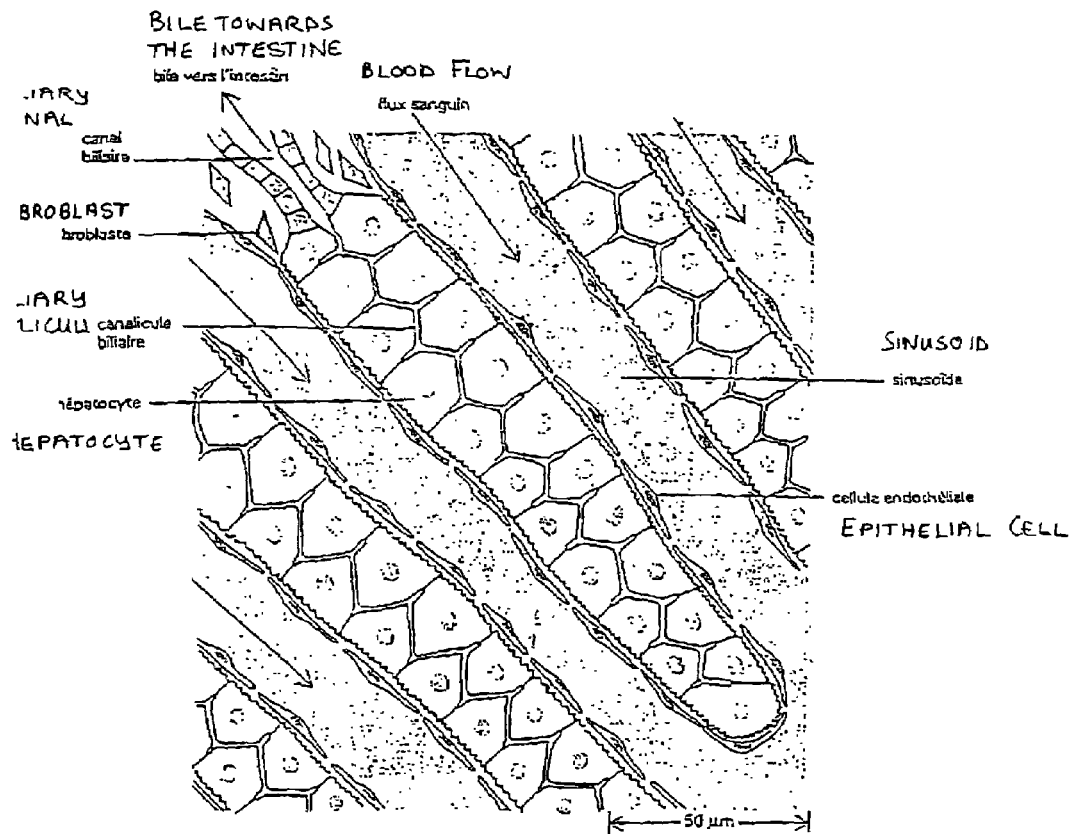

FIG. 2 shows a diagrammatic cross-section of the liver clearly showing the structural organization of the liver cells. In particular, a normal human hepatocyte has the following morphological characteristics:
  These are cells with a granular cytoplasm due to the fact that they are rich in organites such as mitochondria and rough endoplasmic reticulum vesicles, and a round and regular central nucleus with a very dense nucleolus.
  These cells become grouped and organized into typical trabecula, most often formed from cords of 2 to 4 cells, interlinked by joining structures of desmosome type, and communicating structures of "Gap"-type, and bordered on either side by sinusoids in which the blood circulates. This organization into trabeculae determines the double polarity which characterizes the hepatocyte: a sinusoidal pole on the side of the sinusoids and a biliary pole at the interface of the hepatocytes.

The biliary pole is associated with the detoxification function and more particularly with the elimination of biliary salts. It is a dilated intercellular space, closed by characteristic complex junctions (tight junctions plus desmosomes) which delimit for each cell a specialized membrane zone on the one hand, at the functional level by the expression of specific proteins, and on the other hand, at the morphological level by the formation of numerous villi.

Moreover, the term biliary cells refers to cells constituting the biliary canals and canaliculi. The latter make it possible to evacuate into the bile, the biliary salts originating from the hepatocytes and having circulated along the trabecula of parenchymatous cells via the biliary pole.

Selection of Cells Having a Hepatocyte Morphology

The cells originating from the wells initially selected for their high proportion of hepatocyte-type cells are maintained in a culture medium containing $5.10^{-7}$ M of hydrocortisone hemisuccinate. It is noted that their morphology becomes more and more heterogenous and removed from that of a hepatocyte.

In order to find a hepatocyte-type cell population, in accordance with the invention the following selection method is then used:
  a differentiation medium is used, formed from a basic medium containing only 5 mg/L of insulin and 10% of FCS to which 2% of DMSO and 5.10-5 M of hydrocortisone hemisuccinate are added. Once confluence is well established, the HepaRG cells are cultured in this medium.

In the following 2 to 4 days, the medium, which is highly toxic, causes the death of more than 90% of the cells. In parallel, the morphology of certain surviving cells changes considerably.

After two weeks of this treatment, the mortality rate of the cells appears to be zero, and certain surviving cells have the same morphology as normal human hepatocytes, cultured under the same conditions.

It is therefore established that the differentiated cells are more resistant to DMSO than the others.

The cells, once replaced in the medium without DMSO, return to an active proliferation phase.

The selection process is continued. After 3 selection stages in this differentiation medium, most of the cells become resistant to DMSO and capable of re-differentiating, once confluence is reached.

The homogeneity of the population is further increased by means of two other selection protocols.

We observed and took advantage of the fact that treatment with trypsin tends to separate the most differentiated cells in the form of multi-cell clusters whilst the less differentiated cells are isolated. The purification of the large aggregates makes it possible to enrich the population with cells capable of differentiating.

The use of collagenase is based on a very different principle: the treatment carried out with the collagenase involves selective separation of the most differentiated cells which can be recovered and reseeded.

Finally, the stability of the phenotype of the line is considerably promoted by the continuous use of a high concentration of hydrocortisone hemisuccinate (5.10-5 M).

Morphological Modifications: from Proliferation to Differentiation

An unexpected characteristic of the cells selected concerns their ability to proliferate in the presence of strong corticoid concentrations. After separation, most of the cells attach to the support in two hours and begin to proliferate. During the exponential proliferation phase, the population doubles in 24 hours then, when the cells reach confluence, growth slows down. The latter reaches a plateau in the 10 days following the passage, after which the cells can no longer divide, but stay alive for several weeks.

Figure 3:
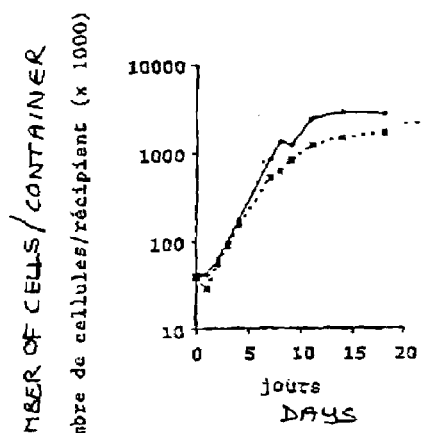

In FIG. 3, the cells cultivated in the absence—■—or in the presence of hydrocortisone ($5.10^{-5}$ M)—◆—for 10 passages were seeded at a density of 40,000 cells per 4 $cm^2$ well and maintained in the same culture medium. The cells were collected by trypsinization and counted manually.

Figure 4:
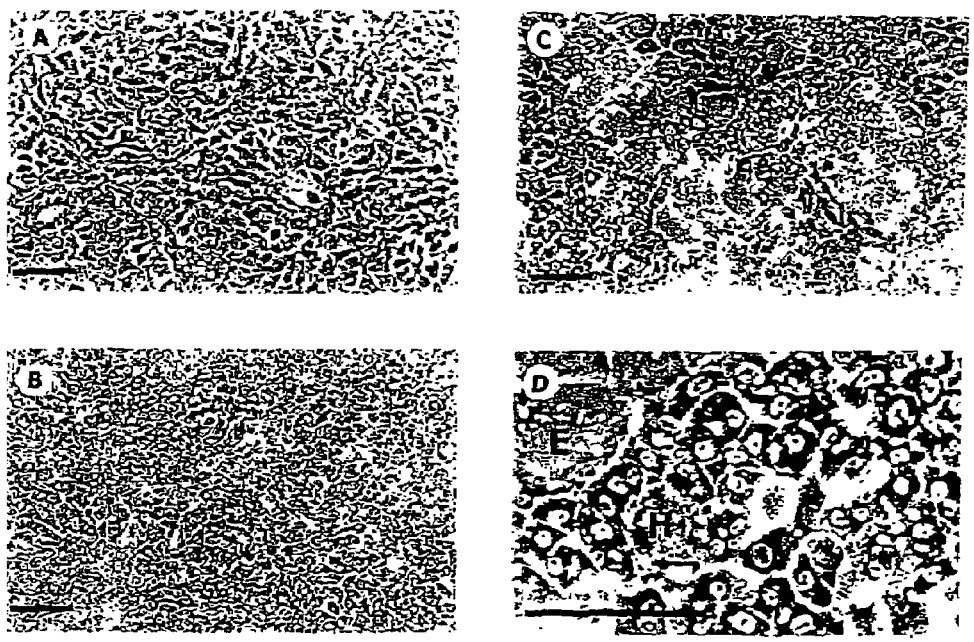

During the proliferation phase, the HepaRG cells form a homogenous population of epithelial phenotype (absence of regular structural organization) and shapes different from that of the hepatocytes (FIG. 4A, HepaRG cells under proliferation conditions). Once confluence is reached, the cells undergo considerable morphological modifications. In four weeks, a number of colonies of granular hepatocyte-type cells appear, whilst at the periphery, epithelial cells can be distinctly seen (FIG. 4B, HepaRG cells maintained at confluence for 20 days). The addition of DMSO two weeks after the passage induces a very complete morphological differentiation: organization of the cells into trabeculae comparable to those obtained in primary culture of normal hepatocytes, in which canaliculus-type structures can be recognized (indicated by a black arrow in FIG. F4). FIGS. 4C and 4D show HepaRG cells maintained at confluence for 5 days, then treated with 2% of DMSO for 15 days (scale=100 μm).

Some epithelial cells occupy the free spaces (flat, regular cells, written in full in FIG. 4C and annotated by the letter E in FIG. 4D). The characteristic hepatocyte morphology is also translated at the level of the organization into trabeculae of the hepatocyte cords. It is obtained at the end of two weeks of exposure to DMSO, the granular cells then very strongly resembling hepatocytes (FIG. 4C, cells annotated by the letter H in FIG. 4D). At the end of these two weeks, no further significant modifications are noted.

The conditions making it possible to obtain complete hepatocyte differentiation are therefore defined by:
one week of confluence in the presence of corticoid ($5.10^5$ M of hydrocortisone),
then two weeks of differentiation in the presence of hydrocortisone and 2% of DMSO.

Surprisingly, it was observed that by selectively collecting the granular cell population from the trabeculae, the latter was capable, even after a long period of quiescence, of returning to the active proliferation phase and once again giving rise to two hepatocyte and epithelial cell types, when confluence is reached.

Figure 5:
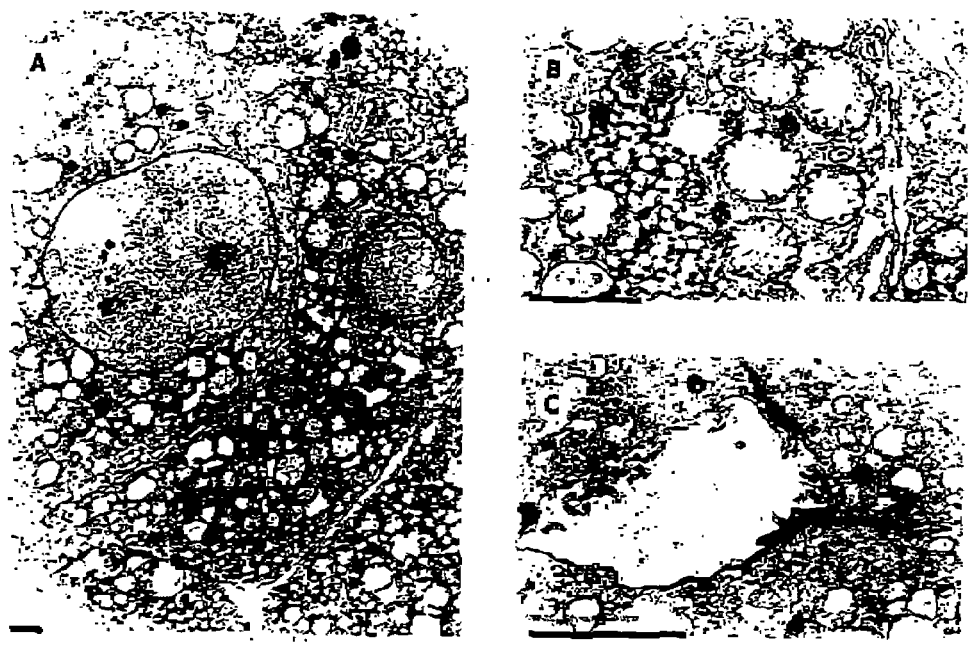
FIG. 5, electron micrographs of HepaRG cells

An electron microscope study revealed the structural organization of the cells: two adjacent cells are strongly attached to each other by desmosomes (FIG. 5A, view with low magnification), with structures strongly resembling biliary caniculi, and surrounded by complexes typical of junctions ("tight" junctions+desmosomes). FIGS. 5B and 5C show views with a greater magnification, showing a typical accumulation of collagen granules and a biliary canaliculus-type structure. (Scale=2 μm).

In FIG. 5A, characteristic regular, round nuclei can be seen, comprising one or two nucleoli. The large number of mitochondria in the cytoplasm are slightly domed in shape, showing a few peaks. It is also possible to observe a number of cytoplasmic granules, which are in fact an accumulation of glycogen particles organized into a "rosette" as described in the normal liver in vivo (FIG. 5B).

Figure 6:
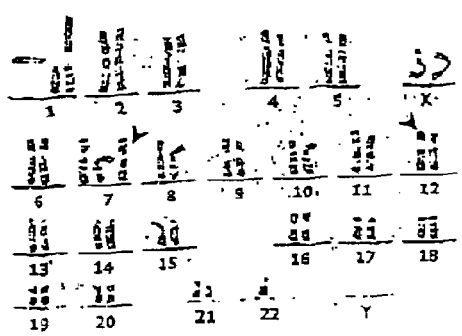
FIG. 6, the karyotype, with RHG-type staining, of a pseudodiploid metaphase representative of the HepaRG line, FIG. 7, a Northern blot analysis of the expression of the mRNAs in 2 liver biopsies, HepG2 cells and HepaRG cells, FIG. 8, the effects of activity inducers CYP1A (phenacetin deethylase) and CYP3A4 (nifedipine oxidase), FIG. 9, the influence of corticoids and DMSO on the level of hepatic mRNAs in the HepaRG cells, FIG. 10, the effects of different factors influencing the infectability of the cells, and FIG. 11, the results of infection of the HepaRG cells with HBV.

Finally, unexpectedly, the karyotype of the cells of the line is subdiploid. The following karotype formula was deduced: 46 <2n>, XX, + del (7) (q11-q21) inv? (7) (q21 q36), -der (22) t (12; 22) (p11; q11). Determination of the deletion and translocation points was carried out by hybridization in situ. Out of 40 mitoses studied, 65% contain 46 chromosomes. 100% of the cells have the following anomalies (FIG. 6):
a supernumerary and modified chromosome 7 leading to a trisomy 7, and
a translocation t (12.22) with a loss of the fragment 12p leading to a monosomy 12p (FIG. 6).

Other isolated anomalies were detected and are reported in Table I below:

TABLE 1

Cytogenetic Characteristics of the HepaRG Line
CHROMOSOMES WITH ANOMALIES

| CHROMOSOME | ANOMALIES | | FREQUENCY (% OF MITOSES) |
|---|---|---|---|
| 7 | ?inv(7)(q21q36) del(q11-q21) supernumerary | Partial trisomy | 100 |
| 12 | Unbalanced translocation | Monosomy 12p | 100 |
| 22 | t(12; 22)(p11; q11) | Monosomy 22p | 100 |
| 2 | supernumerary | Trisomy | 15 |
| 4 | supernumerary | Trisomy | 7.5 |
| 8 | i(8)(q10) | Monosomy 8p Monosomy 8q | 5 |

EXAMPLE 2

Functional Ability of the Line

1. Materials and Methods

Extraction of the RNA and Analyses
THE total cell RNA is extracted using the Total SV RNA® kit; (Promega, France), separated on 1.5% agarose gel and analyzed by Northern blot. A check on the quantity of RNA transferred to the filters is carried out after staining with methylene blue.
The hybridization is carried out according to the protocol of Gripon et al. (1993, Virology, 192: 534-540).

Enzyme Activities Associated with the Detoxification Function
The enzyme activities were established by means of the protocols developed by Guillouzo et al. (1993, Hepatology 18: 406-414).
The following were studied:
the deethylation of phenacetin to paracetamol,
the oxidation of nifedipine to 3, 5-dimethoxy-carbonyl-2, 6-dimethyl-4-(2-nitro-phenyl) pyridine,
the demethylation of dextromethorphan to dextrorphan tartrate,
the hydroxylation of tolbutamide to hydroxytolbutamide,
the hydroxylation of 4-mephenyloin to 4-hydroxymephenyloin.
For comparison, enzyme activities were also determined on cultures of normal human hepatocytes incubated for 2 to 16 hours in the presence of the following substrates:
$2.10^{-4}$ mol/L of phenacetin
$2.10^{-4}$ mol/L of nifedipine
$2.10^{-4}$ mol/L of dextromethorphan and mephenyloin
1 mmol/L of tolbutamide.
The assays are carried out by high performance liquid chromatography (HPLC). The results are expressed in picomoles of metabolites formed per hour and per μg of DNA. The activity of the glutathion-S-transferase (GST) is estimated using 1-chloro-2, 4-dinitro-benzene (CDNB) (Merck) as substrate, at pH 6.5 and at ambient temperature.

2. Results
The level of differentiation of the cells was checked by analysis of the quantities of different mRNAs specific to the liver, in particular the mRNAs of the proteins of the functions specific to the liver, such as the proteins of the serum (albumin, transferrin), a hepatic enzyme involved in glycolysis (aldolase B) and 3 specific enzymes involved in detoxification (CYP2E1, CYP3A etGSTa). All these RNAs are expressed by adult hepatocytes.

Their expression levels in the proliferation and differentiation phases were compared. Moreover, a comparison was established with the corresponding expression levels in human hepatocytes and the HepG2 cells.

Figure 7:
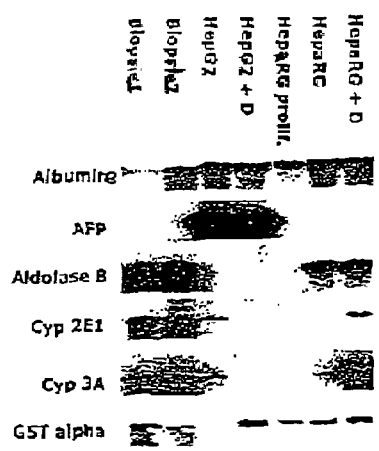

FIG. 7 is a Northern blot analysis of the expression of the messenger RNAs in 2 liver biopsies, HepG2 cells and HepaRG cells. The cells were maintained either under proliferation conditions (prolif) or at confluence for 1 month. Treatment of the cells with 2% of DMSO for the last 15 days of culture is indicated as follows: +D.

Little or no specific hepatic mRNAs were detected in the cells during proliferation. In contrast, these can be detected in the cells at confluence, maintained for 2 weeks in the presence of a high corticoid concentration. Those of albumin and aldolase B are strongly expressed, whereas CYP2E1 and CYP3A4 remain weakly expressed. It is also observed that in the cells having acquired the typical organization into trabeculae, exposure to DMSO causes an increase in the transcripts corresponding to the increased expression of the latter two enzymes, making their expression level practically equal to that observed in cells originating from biopsies.

The study carried out in parallel on cells of the HepG2 line used as a reference reveals that 3 of the 5 specific functions studied are only slightly expressed or not expressed in these cells. Moreover, the action of the DMSO on the HepG2s seems to inhibit the expression of certain of these functions, in particular CYP2E1 and CYP3A.

These analyses demonstrate the original character of the HepaRG line.

The activity of these different enzymes corresponding to detoxification phases I and II was then measured. The other cell lines weakly express these enzymes, often late, or also do not respond to specific inducers.

Figure 8:
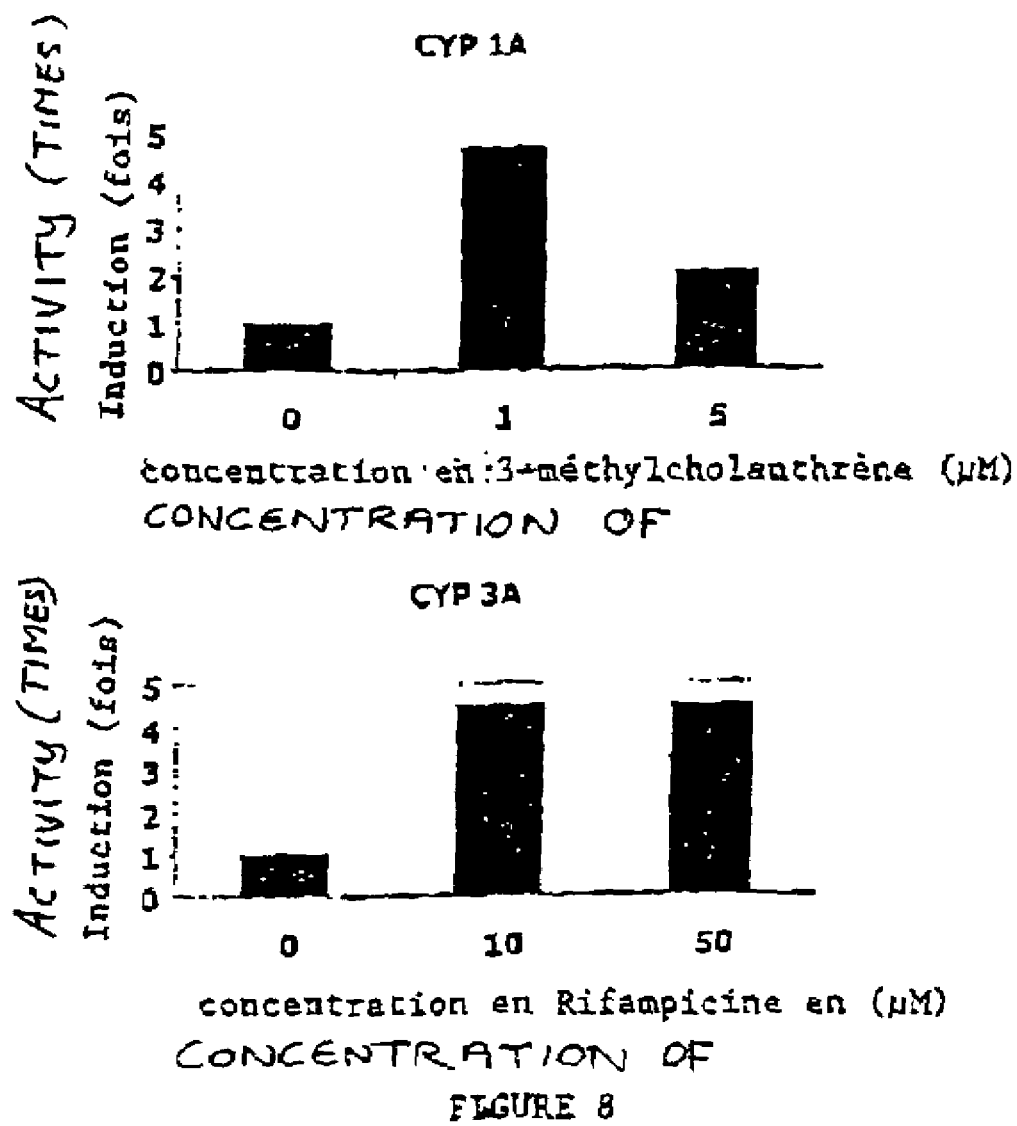

The activity of these different enzymes was measured on confluent HepaRG cells treated with DMSO. This activity was compared to that of primary cultures of human hepatocytes, as well as to that of the HepG2 lines and the BC2 clone of the HBG line. The results are given in Table II below:

Examination of this table shows that the HepaRG cells possess the enzyme activities associated with the detoxification function at levels practically equivalent to those expressed by normal human hepatocytes, except for dextromethorphan demethylase, the activity of which is slightly less. Activation of the phenacetin deethylase and nifedipine oxydase is greater than that obtained with the other lines. This activation is lower than that observed in normal human hepatocytes, whilst remaining within the same order of magnitude (FIG. 8, the activities were measured after 72 hours of treatment and are expressed as a ratio of the cells treated to the cells not treated corresponding to the control cells).

EXAMPLE 3

Cooperation Necessary Between the Corticoid and DMSO for Complete Differentiation Experiments were carried out in order to verify whether both agents were necessary to induce complete differentiation.

1. Effect on the Differentiation

A first series of experiments was carried out in order to study the effects of the absence of the corticoid on cells having always been maintained in its presence. In FIG. 9A, the HepaRG cells at passage 13, were kept for 2 additional passages either in the continuous presence of hydrocortisone (growth: HN), or in the absence of hydrocortisone (growth: HO). They were then induced to differentiate (diff.) for 3 weeks in the absence of hydrocortisone (HO) or in the presence of hydrocortisone $5 \times 10^{-5}$ M (HN), and in the presence of different concentrations of DMSO.

The withdrawal of the corticoid was carried out at confluence, i.e. at the time when the cells begin their differentiation.

After culture for 2 weeks, in the absence of DMSO, no specific liver function (no transcript), except albumin, is detected. The addition of 2% of DMSO is so toxic that its use is impossible. The addition of 1% of DMSO, less toxic, does not induce any more advanced differentiation.

A second series of experiments made it possible to study the effects due to the absence of DMSO.

When the cells are exposed only to corticoid, the presence of a few transcripts (of albumin, transferrin and aldolase B) is

TABLE II

Activity of the Enzymes of Phases I And II

| ENZYME ACTIVITY | HUMAN HEPATOMA LINE | | | PRIMARY CULTURE OF HUMAN HEPATOCYTES | | |
|---|---|---|---|---|---|---|
| | HepaRG | HBG BC2 | HEPG2 | Min/Max | Average | n |
| Phenacetin deethylase* | 0.33 | 0.1 | 0.3 | 0.1-25 | 3.9 | 47 |
| Tolbutamide hydroxylase | 0.51 | 0.03 | <0.2 | 0.2-2.1 | 0.9 | 8 |
| S-mephenytoin hydroxylase* | 0.45 | <0.1 | ND | 0.1-2 | 0.7 | 10 |
| Dextromethorphan demethylase* | 0.06 | 0.02 | <0.1 | 0.1-2 | 0.5 | 10 |
| Nifedipine oxydase* | 1 | 1 | <0.5 | 0.5-30 | 5.7 | 34 |
| Paracetamol glucuronyl transferase* | 3.7 | 1.5 | <0.3 | 0.3-16 | 4.1 | 26 |
| Paracetamol sulphoconjugation* | 0.7 | 0.16 | 0.3 | 0.1-14 | 3.6 | 27 |
| Glutathion S-transferase+ (substrate: chlorodinitrobenzene) | 0.04 | 0.008 | ND | 0.03-0.5 | 0.12 | 27 |

*activity expressed in nanomoles of metabolites produced/h/mg of proteins
+activity expressed in units/mg of proteins detected at very low levels. The addition of 1 to 2% of DMSO to the culture medium causes a rapid accumulation of a number of transcripts, in particular those already mentioned and those of CYP2E1 and CYP3A.

This demonstrates that the cooperation between the corticoid and the DMSO is indispensable in order to reach maximum differentiation. Finally, the stability of the cultures was established over at least 6 weeks.

2. Effect on Proliferation: Continuous Use of Corticoid

The cells are kept in a culture medium without corticoid and their ability to carry out differentiation is tested after 2 (FIG. 9A) and 10 passages (FIG. 9B).

In both cases, no differentiation is observed and only the mRNA of the albumin is detected. The addition of 2% of DMSO proves highly toxic and the addition of 1% of DMSO causes no perceptible changes.

The addition of corticoid only at confluence, on the other hand, causes an accumulation of the different transcripts specific to the liver. But this differentiation is incomplete as the CYP2E1 and CYP3A transcripts are difficult to detect, even after the addition of 1 or 2% of DMSO, the latter dosage proving to be highly toxic after 10 weeks without corticoid.

Finally, the cells without corticoid gradually undergo growth modifications: contact inhibition is delayed to the extent that the confluence plateau has a cell density twice that noted with cells continuously maintained in the presence of corticoid (FIG. 3).

This study clearly shows the importance of the cooperation between the DMSO and the corticoid, both in the proliferation phase (the corticoid making it possible to reduce the toxicity of DMSO) and in the differentiation phase (where the action of the two agents is complementary).

EXAMPLE 4

Abilities of the HepaRG Cells to Evolve Towards the Biliary and Pancreatic Differentiation Routes 1. Materials and Methods HepaRG cells were separated, diluted to ⅕ in Williams' E medium to which 5 µg/ml of insulin, 100 U/ml of penicillin, 100 µg/ml of streptomycin, 510-5M of hydrocortisone hemisuccinate, 2 mM of L-glutamine and 10% FCS were added, then redistributed into wells with a plastic support. Four culture conditions were produced:

HepaRG cells were treated with 3.75 mM sodium butyrate in the maintenance medium as from the day following subculture according to the protocol described by Blouin et al. (1995, *Specialization switch in differentiating embryonic rat liver progenitor cells in response to sodium butyrate*, Exp. cell res., 217: 22-33). The medium is then replenished every 2-3 days, the HepaRG cells were treated 5 days after subculture by 3.75 mM sodium butyrate or 2% DMSO. The medium was replenished every day for 5 days, the HepaRG cells were treated at strong confluence by 3.75 mM sodium butyrate; the medium was replenished every 2-3 days, the HepaRG cells were seeded on a plastic support or monolayer of rat primitive biliary epithelial cells in MEM alpha medium complemented with L-glutamine (2 mM), i-inositol (0.2 mM), folic acid (20 mM), β-mercaptoethanol ($10^{-4}$ M), transferrin 200 µg/ml, 12.5% FCS and 12.5% horse serum. In certain situations, cytokines such as LIF, IL-3, SCF or G-CSF were added to the medium. This medium was replenished every 2-3 days.

Indirect Immunohistochemistry

The cells after washing with PBS are fixed by a solution of 4% paraformaldehyde buffered by 0.1 M sodium cacodylate at pH 7.4 for 20 minutes at 4° C. They are then preserved in a PBS buffer until the time of the analysis.

The specific sites are saturated for 45 minutes with PBS containing 10% FCS. The samples are then treated with primary antibodies for an hour at ordinary temperature in PBS containing 0.05% saponin. After 3 washings in PBS containing 0.05% saponin, the samples are incubated with the second antibody coupled to peroxydase. Two washings are then carried out, then the peroxydase activity is revealed by incubation with 0.4 mg/ml of 3,3'-diaminobenzidine in a solution of 0.05M Tris at pH 7.6, 0.01% $H_2O_2$ at 110 volumes.

2. Results a/ Differentiation Towards the Biliary Route (FIG. 12)

Morphological Modification

Before any treatment and at confluence, the HepaRG cells constitute a population which is not very homogenous, where polygonal cells and elongate cells are found (FIG. 12).

Under all the conditions of treatment at confluence of the HepaRG cells by the sodium butyrate, the cells have the particular morphology of biliary cells in culture (FIG. 12). The cells spread out and increase in size, they have a clear cytoplasm with an ovoid nucleus containing several nucleoli. The contour of the cells is generally poorly defined. Sometimes, lipid droplets are observed. When the cells are treated at very strong confluence, certain of the cells die. These cells probably correspond to the cells already committed towards the hepatocyte route.

The effect of the butyrate was also tested on HepaRG cells at a low density and in active proliferation phase. A characteristic of these cells is their ability to proliferate in the presence of a high dose of sodium butyrate (FIG. 13A).

During the proliferation phase, the HepaRG cells form a homogenous population of epitheloid-type cells, at confluence they have the appearance of biliary epithelial cells.

Phenotypical Changes

The morphological modifications observed in the presence of sodium butyrate are correlated to phenotypical changes (Blouin et al. 1995). We used four markers of differentiation towards the biliary route, γ-glutamyl transferase, the α6 chain of integrins and the cytokeratins 7 and 19 which normally disappear when the cells are directed towards the hepatocyte route. For differentiation towards the hepatocyte route, we looked for an increase in the expression of albumin and a reduction in the expression of the al chain of the integrins.

In the first instance we characterized the non-differentiated proliferating cells. The cells of the HepaRG line have the following phenotype: expression of the c-kit, cytokeratins 7 and 19, α1 and α6 chains of the integrins, γ-glutamyl transferase and albumin suggesting that these cells are oval cells and/or stem cells (see diagram FIG. 1).

When the cells are cultured in the presence of sodium butyrate, they express γ-glutamyl transferase more strongly, preserve the expression of the α6 chain of the integrins, and the cytokeratins 7 and 19 attesting to their commitment towards the biliary route.

When they are cultured in the presence of DMSO, which induces hepatocyte differentiation, we observe a disappearance of the expression of the cytokeratins 7 and 19, α6 chain of the integrins. They express the α1 chain of the integrins at a lesser level and albumin very strongly, confirming their hepatocyte differentiation. The cell populations being heterogeneous in the cultures, these highly characteristic phenotypes are found only in the plaques differentiating towards one or other of the routes.

The results obtained after in situ marking of the cells treated or not treated by sodium butyrate are summarized in Table III below.

TABLE III

Biliary/Hepatocyte Route Differentiation

| | HepaRG cells before treatment | HepaRG cells 2% DMSO Differentiation hepatocyte route | HepaRG cells Sodium butyrate Differentiation biliary route |
|---|---|---|---|
| γ-glutamyl transferase | + | −/+ | ++ |
| α6 chain | + | − | + |
| Cytokeratin 7 | + | − | + |
| Cytokeratin 19 | ++ | − | ++ |
| Albumin | −/+ | ++ | −/+ |
| α1 chain | ++ | + | −/+ |

−/+: weakly positive;
+ positive;
++: highly positive b/ Differentiation Towards the Pancreatic Route (FIG. 13B)

Figure 1:
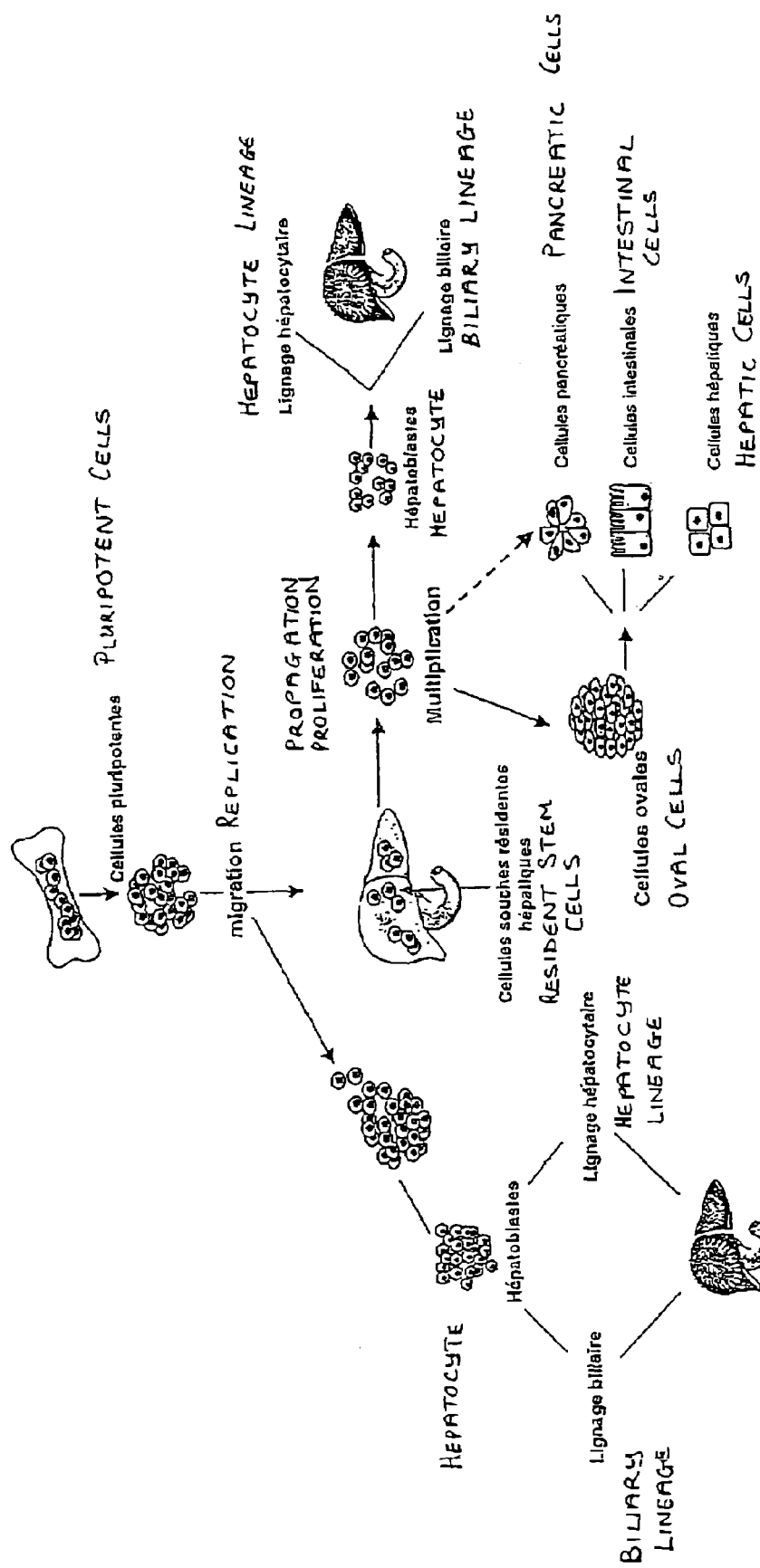
FIG. 1, a diagrammatic representation of the different cell types participating in the homeostasis of the liver, FIG. 2, a diagrammatic cross-section of the liver, clearly showing the structural organization of the different cells constituting the liver, FIG. 3, the growth curve of the HepaRG line, FIG. 4, phase contrast microphotographs of HepaRG cells at different stages of differentiation.

As illustrated by the diagram in FIG. 1, the "oval" stem cells of the liver are pluripotent. Apart from being able to differentiate into hepatic cells, which is demonstrated above, they have the ability to differentiate into other cell types, including the pancreatic cell of the acini. We researched whether this differentiation potential was one of the characteristics of the HepaRG line.

When the cells are seeded and cultured in MEM alpha culture medium, the cells adhere, then retract in order to former spheroid structures suggesting the formation of complex canalicular networks, morphologically similar to the three-dimensional cultures of pancreatic epithelial cells (Keer-Conte et al., 1996, *Ductal cyst formation in collagen-embedded adult human islet preparations: a means to the reproduction of nesidioblastosis in vitro*, Diabetes, 45:1108-1114).

EXAMPLE 5

Infection of the Line by the HBV

1. Materials and Methods

Infection

The infectious source is preferentially constituted by the supernatant of HepG2 cells of the clone 2.2.15, concentrated 100 times. In fact, this infectious source has the double advantage of being inexhaustible and of constant quality.

The cells used for the infection are cells having been cultured according to the conditions defined in Example 1 (permanent presence of $5.10^{-5}$ M of hydrocortisone hemisuccinate) and having been maintained for a week at confluence, then for 2 weeks in the same medium with 2% of DMSO added.

These cells are incubated with the infectious source, diluted 10 times, in the culture medium with 4% of PEG 8000 (Sigma) added, for 20 hours at 37° C. The second part of this HBV infection protocol was established by Gripon et al., 1993, *Virology*, 192: 534-540.

The control cultures were incubated with 4% of PEG and 25% of FCS diluted in a solution of phosphate buffer saline (PBS).

At the end of the incubation, the cells are washed three times with culture medium and maintained in the presence of 2% of DMSO and $5.10^{-5}$ M of hydrocortisone hemisuccinate until they are used.

Neutralization tests were carried out before infection by incubating the virus with hepatitis B surface monoclonal antibodies (S39-10) for 1 hour at ambient temperature.

Detection of the Hepatitis B Virus Surface Antigen (HbsAg)

The HBs antigen was detected in the medium using the ELISA kit (Monolisa AgHBs plus®) from Biorad Laboratories. The results are expressed in pg/ml of supernatant.

Extraction of Viral DNA and Analyses

Viral DNA replication intermediates were isolated in all the cell lysates. The cells are recovered after separation with trypsin, then lysed at 37° C. with a lysis buffer (10 mM of Tris-HCl pH 7.4, 0.5% of SDS, 10 ml of EDTA pH 7.4, 10 ml of NaCl) with proteinase K (200 μg/ml) added. The cell DNA is precipitated over 12 hours, at 4° C. with 1M NaCl. The supernatant containing the viral DNA is then extracted. The complete viral particles are isolated from the cell supernatant by immunoprecipitation with an anti-HBs polyclonal antibody (Dako, France). The nucleic acids are finally extracted after 12 hours of lysis at 37° C., in a lysis buffer with tRNA (40 μg/ml) and proteinase K (200 μg/ml) added.

In all the above protocol, the DNA is extracted using phenol-chloroform and precipitated by isopropanol.

The nucleic acids are analyzed by Southern blot on a 1.5% agarose gel. The molecular weight markers are restriction fragments of the DNA of the hepatitis B virus (3182 and 1504 bp). The hybridization is carried out according to the protocol of Gripon et al. above.

2. Results

Evidence of the Infection

The intracellular viral DNA is analyzed over the 10 days following the infection.

Figure 10:
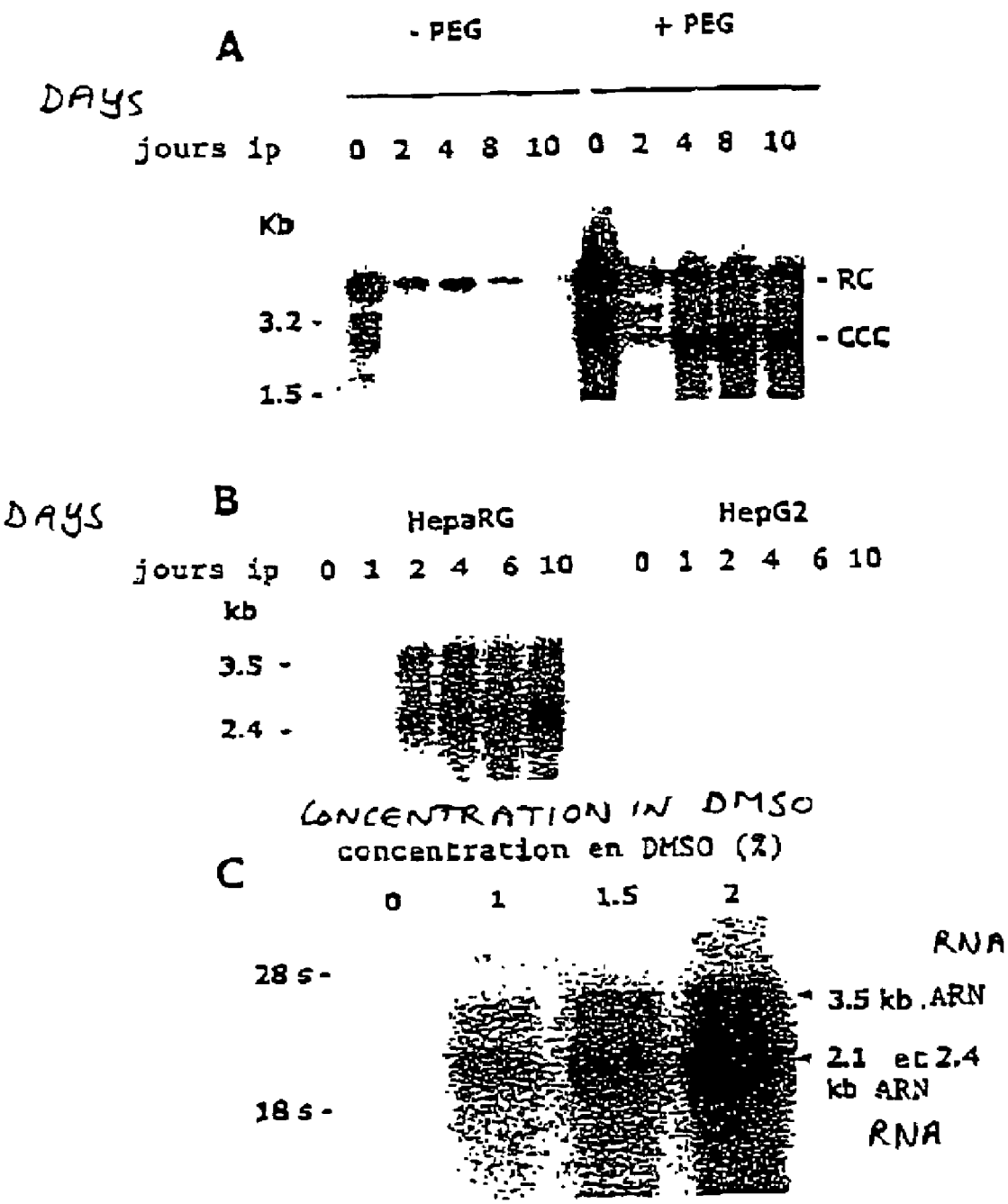

FIG. 10A shows the effects of PEG on the infectability of the cells. It is a Southern blot analysis of the kinetics of appearance of the intracellular viral DNA after infection of the HepaRG cells in the presence of 5% of PEG (+PEG), or in the absence of PEG (−PEG). The position of the relaxed circular (RC) DNA and covalently closed circular (CCC) DNA forms are indicated to the right of the figure. The migration position of the molecular weight markers (fragments of the genome of the hepatitis B virus) is indicated to the left of the figure.

In the absence of PEG, the DNA profile observed is identical to that revealed for the viral particles present in the inoculum.

However, this signal gradually disappears until becoming practically undetectable 10 days after the infection. Moreover, no intermediate form of viral replication is detected under these conditions. On the other hand, the latter are clearly present when the cells are infected in the presence of PEG. A strong signal is observed immediately after the infection, with a profile similar to that observed in the absence of PEG. This proves that the penetration of the viral particles into the cells is effective. On the second day, the signal is sharply reduced due to the elimination of numerous viral particles, but a fine band positioned towards 2 kb can be observed. This band corresponds to CCC DNA (covalently closed circular DNA). The signals detected at intermediate positions correspond to nascent viral DNA, gradually increasing until the 10th day.

In parallel, the kinetics of viral RNA accumulation is established. FIG. 10B is a Northern blot analysis of this kinetics after infection of the HepaRG cells, the HepG2 cells are used as a negative control of the viral infection. The size of the RNAs is indicated to the left of the figure.

The signals at 2.4 and 3.5 kb, corresponding to the main species of RNA specific to the HBV, appear after two days of infection and accumulate only in the infected cells.

In order to verify the specificity of the HepaRG cells to be infected, infection of two other hepatoma lines, HepG2 and BC2, was carried out under identical conditions. These two lines were selected because they are capable of differentiating. They were cultured under conditions allowing them to reach a maximum differentiation stage, as well as under the same conditions as those used for the HepaRG cells. After approximately 12 hours of incubation with the viral particles and 5% of PEG, the intracellular viral DNA and the viral RNA produced are analyzed. Immediately after infection, a large quantity of viral DNA is detected in all the lines, and above all in HepaRG and BC2. To the extent that the trypsin/EDTA treatment eliminates the viral particles adsorbed at the surface of the cells, the DNA observed must correspond to viral particles having penetrated to the interior of the cells. The signal decreases considerably in the two days following the infection. On the other hand, 18 days after the infection, only the HepaRG line has forms corresponding to viral replication intermediates i.e. the ccc DNA and the viral RNA forms. This shows that only the HepaRG line is capable of being infected and initiating the replication of the virus.

The production of viral particles was sought in the supernatant of the infected HepaRG cells. The HBs antigen was assayed by radioimmunology. FIG. 11A represents a kinetics of AgHBs secretion in the supernatant of the cells infected. The supernatants were collected for 15 days after the infection of the HepaRG cells (■), HBG BC2 (■) and HepG2 (□).

A high HBs antigen concentration was detected in the supernatant. The antigen concentration increased during the 9 days following the infection, and was then maintained at a high level. On the other hand, in the supernatant of the HepG2 et BC2 cells, the antigen was only detected in the two days following the infection, which shows that the viral particles were adsorbed by the cells, then gradually released into the medium.

Moreover, the complete viral particles present in the medium were estimated by immunoprecipitation with an anti-HBs antibody, followed by a Southern blot analysis of the DNA present in the precipitate. FIG. 11B shows this Southern blot analysis of the appearance kinetics of the extracellular viral DNA in the supernatant of the HepaRG cells infected by the HBV. After immunoprecipitation of the complete viral particles with an anti-HBs antibody, the viral DNA is extracted, then analyzed. The migration position of the molecular weight markers (fragments of the genome of the hepatitis B virus) is indicated to the right of the figure.

A strong signal is observed two days after the infection. On the 4th day, it has decreased considerably but it gradually increases again until the 8th day and is maintained throughout the culture period. This kinetics analysis is suitable for the method of replication of the virus: after a period of release of the viral particles having penetrated the cell (for 2 to 4 days), the virus begins to replicate actively. The profile observed differs slightly from that obtained on the 2nd day.

In Vitro Neutralization of the Infection

In order to determiner whether a specific anti-S monoclonal antibody is capable of neutralizing the infection of the cells, virions are incubated with variable concentrations of antibodies, then brought into contact with the cells. The residual infection is estimated as a function of the long-term secretion of HBs antigen.

FIG. 11C shows this viral neutralization test in vitro. The viral particles are incubated with seriated dilutions of a monoclonal antibody directed against the Hbs antigen (antibody S 39-10) (■) or of a non-relevant antibody (■) and their infectivity evaluated on the HepaRG cells. The level of infection of these cells is estimated by measuring the secretion of HBs antigen in the supernatant of the cells infected, 10 days after the infection.

In this figure, it can be seen that concentrations of 10 and 1 μg/mL block the viral infection, whilst lower concentrations only induce partial inhibition. A 50% inhibition corresponds to a concentration of 0.03 μg/mL.

Influence of the Degree of Differentiation on the Infection

The ability of the HepaRG cells to be infected was studied as a function of their degree of differentiation. Using the methods described in Examples 1 and 2, the cell differentiation programme was modified.

A first series of infection was carried out on cells continually maintained in the presence of corticoid only, then in the presence of corticoid and different concentrations of DMSO, in order to induce different stages of differentiation.

The analyses carried out 2 weeks later on the viral RNA show a correlation between the accumulation of the two main viral transcripts and the level of differentiation.

FIG. 10C shows the effects of hepatocellular differentiation on infection by HBV. It is a Northern blot analysis of the intracellular viral RNAs after infection of the HepaRG cells in the presence of increasing concentrations of DMSO.

This correlation was confirmed by a series of experiments carried out on cells infected at confluence (before their differentiation) then placed under optimum conditions in order to induce their differentiation. The results are given in Table IV below:

TABLE IV

Effect of Hydrocortisone Hemisuccinate and Cell Proliferation on the Infectability of HepaRG Cells

| Culture | HbsAg secretion (pg/ml)# | | | |
|---|---|---|---|---|
| conditions | | | HN | |
| Differentiation | HO | | HN with 2% | |
| conditions Infection | HO after 17th day | HO after 17th day | HN after 17th day | of DMSO after 17th day |
| D3 (growth) | <20 | <20 | 33 | 41 |
| D5 (growth) | <20 | <20 | 37 | 84 |
| D10 (confluence) | <20 | <20 | 93 | 171 |

HbsAg secretion measured in the supernatant of the cells 47 days after seeding

Examination of this table shows that these quantities of HBs antigen measured are low when the cells are infected before treatment by DMSO, which means that an infection carried out on slightly differentiated cells is not very effective compared with that carried out on strongly differentiated cells. Similarly, an infection carried out on cells maintained in a medium without corticoid (for 10 passages), then cultured for two weeks in the presence or absence of DMSO, also proves to be ineffective, in particular, for cells not having benefited from the action of the DMSO.

Finally, the effectiveness of an infection carried out on undifferentiated cells multiplying actively was compared with that on cells with arrested growth and well-differentiated. The results are given in Table V below:

TABLE V

Effect of Cell Differentiation on the Infectability of HepaRG cells

| Differentiation medium (after day 17) | HbsAg secretion (pg/ml)# | |
|---|---|---|
| | Infection on day 15 day after differentiation | Infection on day 28 after differentiation |
| DMSO 0% | <20 | 31 |
| DMSO 1% | 70 | 214 |
| DMSO 2% | 79 | >2000 |

HbsAg secretion measured in the supernatant of the cells 47 days after seeding

The results show that an infection carried out on cells in the proliferation phase is ineffective, even in the presence of corticoid and of DMSO.

EXAMPLE 6

Use of the HepaRG Line for the Evaluation of the Antiviral Activity of Chemical or Biological Molecules 1. Materials and Methods The cells are maintained and infected according to the protocols of Examples 1 and 5.

The antiviral treatment by 3TC is administered from the 8th day to the 15th day following the infection of the HepaRG cells, at final concentrations of 0.1 and 10 µM in the culture medium. A complete replenishment of the medium is carried out every two days. The supernatants are stored at −20° C. and the cell pellets at −80° C.

The viral antigen (HBs) was detected in the culture supernatant using the commercial ELISA test ETI-MAK-3® (SORIN).

The viral DNA present in the culture supernatant could be detected and quantified by the Amplicor-Monitor test (ROCHE). The results are expressed as number of viral particles/ml. For the analysis of intracellular viral DNA, the cells were separated with trypsin and stored at −80° C. The total DNA was isolated according to the protocol described previously (Zoulim et al., 1998, *Drug therapy for chronic hepatitis B virus replication*. J. Hepatol. 29:151-168).

2. Results

The HBs antigen is detected in the culture supernatant after 8 days of treatment by 3TC, the value remaining constant whatever the dose and equal to the non-treated control.

The Amplicor-Monitor® test demonstrates a dose-dependent reduction in the quantity of viral DNA present in the HepaRG cells infected by the HBV after 8 days of treatment by 3TC, with respect to the control cells infected by the HBV and not treated, as shown by the results of Table VI below.

TABLE VI

| Antiviral Activity of 3TC | |
|---|---|
| 3TC Concentration µM | Inhibition |
| 10 | 100 |
| 1 | 98 |
| 0.1 | 69 |

EXAMPLE 7

Use of the HepaRG Line for the Evaluation of the Antiseptic Power of Products Capable of Inactivating the HBV, for Example Javel Water 1. Materials and Methods
2.
1.1. The HepaRG cells are maintained according to the protocols of Example 1.
1.2. The infection is carried out in parallel:
a) either with a native inoculum obtained as previously described from the HepG2 2.2.15 cells, the infectivity of which is documented according to the operating protocol of Example 5,
b) or with the same inoculum brought into contact with the inactivating solution to be tested, here Javel water.

The antiseptic power will depend on the concentration and period of contact of the product with the inoculum. We tested the Javel water in 2 concentrations: 12° et 24° and two exposure periods: 15 s and 30 s as detailed in the following paragraph.

Exposure of the HBV of the inoculum to Javel water.
series 1: Javel 12° for 15 seconds
" 2: Javel 12° for 30 seconds
" 3: Javel 240 for 15 seconds
" 4: Javel 240 for 30 seconds
" 5: distilled H$_2$O used for diluting the virus: control virus
200 µl of pure virus stock then 200 µl of Javel water are poured into 4 ml tubes. The reaction is stopped by adding 1.6 ml of PBS (dilution 1/10).

Elimination of Excess Javel.

The above viral preparation is decanted into special tubes (2 tubes per series) and ultracentrifuged at 4° C. in order that the HBV is precipitated in the pellet.

The supernatant containing the Javel water is gently drawn off.

The small residual volume of the 2 tubes for each dilution is mixed and the virus pellets recovered by homogenization.

The more or less inactivated viral suspension of each series is inoculated into HepaRG cell cultures according to operating conditions identical to Example 5.

1.3. In order to reveal the infection, both the proteins and the viral DNA will be measured.

The viral Ag (Ag Hbs) is sought by a commercial ELISA test (for example. ETI-MAK-3® from Sorin or also Monolisa Ag HBsplus® from Biorad) as detailed in Examples 5 and 6.

The viral DNA is sought using PCR in the culture supernatant and can be also be quantified by the Amplicor-Monitor® test (ROCHE). The results are expressed in viral genome/ml equivalents. In order to analyze the intracellular viral DNA, the cells are separated with trypsin and stored at −80° C. The total DNA is isolated and the search for DNA specific to HBV is carried out according to the protocol described previously (Zoulim, 1998).

2. Results 2.1. The control inoculum without Javel water makes it possible to obtain production of Ag Hbs and viral DNA in the supernatant as well as the characteristic profiles of the DNA of HBV in the cells, as detailed in Example 5. This infection was obtained with the pure virus and diluted to 1/10.

2.2. With the inoculum exposed to different concentrations of Javel water as described above, it appears that, after contact for 15 or 30 seconds with 12° Javel water, no infection takes place. The same applies to the 24° Javel water (15, 305), for a 1/10 dilution of the virus.

3. Conclusions

The test on HepaRG cells therefore makes it possible for the first time to offer an in vitro infection cell model of the HBV capable of validating physical (heating, irradiation) or chemical procedures (detergent/antiseptic solutions or gases: peroxides, ozone etc.) capable of inactivating this major contaminant virus involved in nosocomial infections via medico-surgical devices and instruments.

In this example, a single dilution was tested. Experiments in progress will specify the sensitivity of the model and the number of logs of infectious doses (expressed as a logarithm to the base 10) that it is possible of evaluate including the capacities of concentrations of the virus by ultracentrifuging/filtration/precipitation.

EXAMPLE 8

Construction of a "cDNA Chip" from the HepaRG Line

This construction comprises the following stages

Preparation of two total RNA pools, then purification of poly A RNA on the one hand, from cells originating from the differentiated HepaRG line after culture in a medium containing $10^{-5}$ M of hydrocortisone hemissuccinate then 2% of DMSO, and on the other hand of non-differentiated cells taken 5 days after subculture.

Preparation of complementary DNAs, by reverse transcriptase.

Carrying out suppressive subtractive hybridization using a commercial kit.

Cloning of the cDNAs present in the subtractive library.

Test of the representativeness of the library by sequencing of a limited number of cDNAs.

PCR amplification of the cDNA products of interest using the universal primers present in the vector.

"Spotting" of the PCR products according to one of the "microarray"-type processes.

Thus the expression of 1000 to 2000 genes representative of functional states of the expression of hepatic cells can be studied in various situations of interest.

EXEMPLE 9

Inoculation and Culture of the Hepatic Forms of *Plasmodium falciparum* in the HepaRG Line A few years ago, it was demonstrated that normal human hepatocytes in primary culture represented a system favourable to the survival of *Plasmodium falciparum* and that the latter could support the complete hepatic cycle of the parasite. In contrast, replication models in the hepatoma cells have to date been lacking.

The novel HepaRG hepatoma line may represent an important advance, due to observation in a test involving infestation of these cells by the parasite, of a complete cycle with formation of schizonts.

Materials and Methods

*P-falciparum* sporozoites are prepared from *Anopheles stephensi* mosquitoes infected by ingestion of blood cells, themselves infected by the erythroid forms of the parasite, the gametocytes.

Approximately two weeks after the infectious meal, the infected salivary glands are dissected under aseptic conditions and collected in culture medium.

These suspensions, i.e. 10 pairs of salivary glands per 100 ml of medium, are added to the cultures of HepaRG cells.

The cells used for the infestation were cultured according to the conditions defined in Example 1 (permanent presence of $5.10^{-5}$ M of hydrocortisone hemisuccinate) and maintained for a week at confluence, then for 2 weeks in the same medium with 2% of DMSO added.

At the time of the infestation, they are confluent and completely differentiated by the corticoid/DMSO treatment described in Examples 1 to 4.

The exposure or inoculation period is approximately 3-4 hours and is carried out in the same medium deficient in DMSO. Then, medium is added to the cultures and replenished every 2-3 days.

Detection of the Parasites

The preparations are washed in PBS then fixed and stained by May-Grunwald Giemsa staining. The intra-cellular parasites have a cytoplasmic localization. The characteristic formation of schizonts appears clearly. These schizonts firstly have a small number of nuclei, then they grow larger, with a considerably increased number of nuclei, attesting to the realization of a complete replication process.

Optimization of the Infestation Protocol

*Plasmodium falciparum*, a very fragile parasite, has appeared highly sensitive to DMSO. The results, showing a greater effectiveness, were obtained by removing the DMSO from the culture medium during the inoculation period.

EXAMPLE 10

Injection of hepaRG Cells into a Mouse

It is possible to inject hepaRG cells into an immunodeficient laboratory animal such as a nude mouse in order to obtain an in vivo study model.

This injection into the mouse allows the hepaRG cells to find an environment favourable to their proliferation and their differentiation, leading to the formation of a large mass of differentiated cells. Given the pluripotent character of the hepaRG cells, these cells will undergo different differentiations depending on the cell implantation site (hepatic, pancreatic cells etc.). This injection thus makes it possible to reconstruct an organ of hepatic or pancreatic type in an animal, having an alteration of said organ (see article of M. Dandry et al., 2001, 33: 981-988, *Hepatology*, Repopulation of mouse liver with human hepatocytes and in vivo infection with hepatitis B virus).

This model not only allows the study of the functions of the human hepatocyte in a whole animal organism but also the study of the infection of human hepatic cells by hepatotropic viruses and/or parasites in an animal model.

EXAMPLE 11

Infection of the Line by the HCV

1. Materials and Methods

Infection

The infectious sources originate from serums of patients infected by the HCV. At present this is the only source of virus available, knowing that to date it has not been possible to develop any virus production model. Five serums were tested. The viruses from two serums (Nos. 2 and 4) have a genotype lb and that of serum No. 3 is a virus of genotype 3. The genotyping was not carried out on the two serums used, it concerns serums No. 1 and No. 5.

The cells used for the infection were cultured according to the conditions defined in Example 1 (permanent presence of $5.10^{-5}$ M of hydrocortisone hemisuccinate) and maintained for a week at confluence, then for 2 weeks in the same medium with 2% of DMSO added.

These cells are incubated for 48 hours at 37° C. with the infectious source, diluted 10 times, in the culture medium devoid of FCS and optionally with PEG 8000 (Sigma) added.

For controls, cultures were incubated under identical conditions but the serum used this time originates from a patient not infected by the HCV.

At the end of the incubation, the cells are washed three times with culture medium and maintained in the presence of 2% of DMSO and $5.10^{-5}$ M of hydrocortisone hemisuccinate until they are used.

Extraction of the Intra and Extracellular Viral RNAs and Analyses

The replicative forms of the intracellular viral RNAs were isolated in all the cell lysates. The cells are recovered after separation with trypsin, then the total RNA is extracted using the High Pure RNA Isolation kit (Roche). The quantity of total RNA extracted is estimated by optical density in order to standardize the different samples. The quality and homogeneity of the RNAs are examined by visualizing the ribosomic RNAs (rRNA: 28S and 18S) on a 1% agarose gel stained with ethidium bromide.

The RNAs of the viral particles are extracted from the culture supernatant using the High Pure viral RNA kit (Roche).

By retrotranscription (RT), the complementary DNA (cDNA) of the viral RNAs of positive polarity is synthesized from a specific prime hybridizing at 5' of the region which codes for the viral capsid protein. This oligonucleotide (5'-TTTGAGGTTTAGGATTYGTGCTCAT-3'), designated as SEQ ID NO:1, derived from that described by Martell et al., 1999, *Journal of Clinical Microbiology*, 37: 327-332 , designated C-342. The cDNA is then amplified by the "Polymerase Chain Reaction" (PCR) technique using two primers hybridizing in the 5' non-translated region of the viral genome. The primers used are as follows: the sense oligonucleotide (5'-TGAGTGTCGTRCAGCCTCC-3'), designated as SEQ ID NO:2, and the antisense oligonucleotide (5'-ACCACAAG-GCCTTTCGCRACCCAC-3'), designated as SEQ ID NO:3, which corresponds to that conceived by Mercier et al., 1999, *Journal of Virological Methods*, 77 1-9, designated NCR-3. The amplification product (amplicon of 190 pb) is visualized on a 2% agarose gel stained with ethidium bromide. A marker of molecular weight of DNA (M) is also deposited in order to verify the identity of the amplicon by its size. The effectiveness of the different stages is always controlled by detecting the viral RNA present in a standard (T+), which corresponds to a diluted serum, originating from an infected patient. The absence of any contamination is also systematically verified in the retrotranscription (RT) and amplification (POR) stages by substituting water (T-) for the samples.

2. Results

Evidence of the Infection

Figure 14:
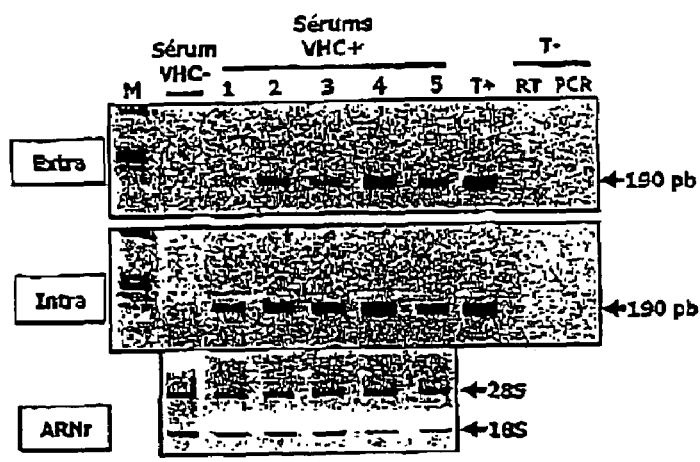
FIGS. 14 and 15, the infectability of HepaRG cells with the serum of patients carrying HCV, in the presence or absence of interferon α, FIG. 16, the kinetics of replication or inhibition of HCV, by interferon α, FIG. 17, the kinetics of infection by parasites of the genus *Leishmania*, and, FIGS. 18 and 19, optimizations of the protocol of infection by parasites of the genus *Leishmania*.

FIG. 14 shows the analysis of the infectability of the HepaRG cells by viruses originating from the five serums tested. This involves looking for the presence of the viral RNA both in the extracellular and intracellular compartments by RT-PCR after infection of the cells in the presence of PEG 8000. The viral RNA is sought on the 12th day following the infection. The position of the amplicon is indicated to the right of the figure. The rRNAs are shown after homogenization of the samples in the lower part of the figure where the position of the 28S and 18S RNAs is indicated on the right.

During the use of a inoculum without any virus (HCV-serum), no viral RNA is detected either in the culture supernatants or in the cells. Despite the origin of the line which was selected from a liver tumor taken from a female patient suffering from viral hepatitis C, no residual viral replication is detectable in the HepaRGs.

The semi-quantitative technique of detection by RT-PCR makes it possible to reveal the presence of signals not only in the intracellular compartment but also in the culture supernatants whatever the serum used (serums No. 1 to No. 5). These results explain the establishment of an HCV replication in the HepaRG cells which leads to an effective secretion of virions by the cells.

In order to confirm that a viral replication is established in the HepaRG cells after their infection, the sensitivity of the HCV replication to an antiviral, interferon α, was studied. The cells were inoculated over 48 hours in the presence of PEG 8000 by the virus-containing serum No. 4. A serum without any HCV is used as a negative control of the viral infection. Cytokine (Introna®, Schering-Plough, France) is added to the culture medium from the end of the 6th day to the 12th day following the infection of the cells, at final concentrations of 5, 50 or 500 U.I./ml. Complete replenishment of the medium is carried out every two days. The supernatants are stored at −80° C. for kinetics analysis.

Figure 15:
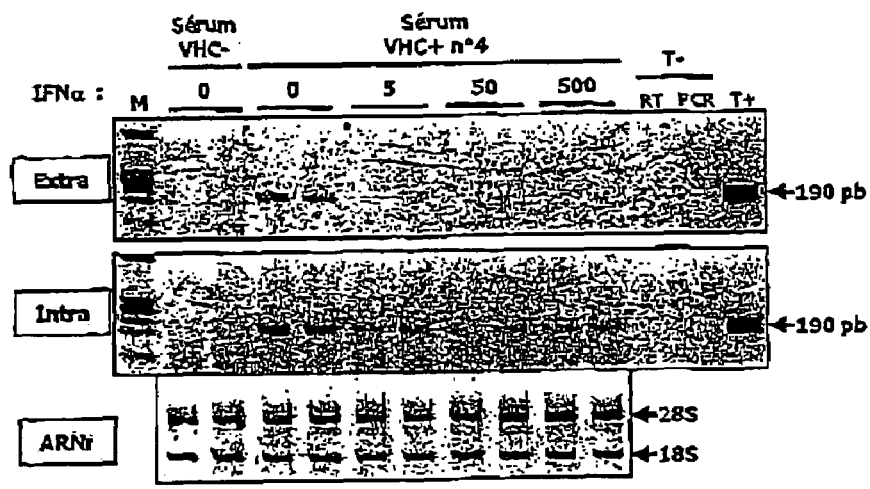

FIG. 15 shows the incidence of the presence of the interferon α on the 12th day following the exposure of the cells to the infectious source, with respect to the quantity of viral RNA detectable in the cells and in the supernatants. The position of the amplicon is indicated to the right of the figure. The rRNAs are shown after homogenization of the samples in the lower part of the figure where the position of the 28S and 18S RNAs is indicated on the right. Starting from the lower dose (5 U.I./ml), a drop of more than 60% of the intracellular signal is detected after the six days of treatment and complete disappearance of the signal is obtained in the extracellular medium.

Kinetics of HCV Replication and Its Inhibition by Interferon α

Figure 16:
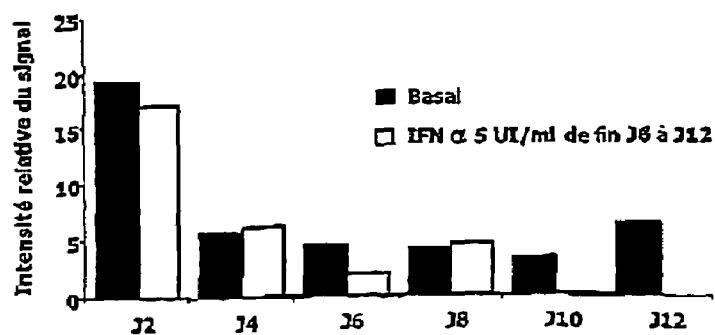

A kinetics of HCV replication and of its inhibition by interferon α was established and is shown in FIG. 16. The presence of the viral RNA in the supernatants was sought in parallel in a non-treated reference culture (v) and in a culture where the cytokine is present in the medium at 5 U.I./ml a concentration the effectiveness of which was previously verified (FIG. 15), from the end of the 6th day following the infection, until the 12th day after exposure to the infectious source (o).

Analysis of the sample taken at the end of the 2nd day following the infection (v, Day 2) reveals a strong signal. This phenomenon must correspond to a release from the inoculum of the viruses which were initially adsorbed onto, or internalized in, the cells. Then, the constant signal detected from the 4th day post-infection (υ, Day 4 to Day 12) translates an active replication of the virus which leads to a constant secretion of virions over the period studied. The first part of the kinetics carried out on the cultures incubated in the presence of interferon α is identical to that carried out in the absence of the antiviral (compare υ and o from Day 2 to Day 8). This makes it possible to affirm that a replication was well established in the HepaRG cells before the treatment. In contrast, after four days of incubation with cytokine, no extracellular viral RNA is detected, until the end of the treatment (o, Day 10 to Day 12). The inhibitory action of interferon α observed in vivo is therefore well reproduced in the HepaRG cells infected by the HCV, after a minimum treatment period of 2 days.

EXAMPLE 12

Infection of the Line by Parasites of the Genus Leishmania

The *leishmaniases* are diseases subsequent to infection by a parasite of the genus *leishmania*. The clinical presentation of these infections ranges from localized cutaneous infection, to a disseminated infection during which the main organs infected are the lymph glands, bone marrow, spleen and liver. The *leishmania* are transmitted in flagellate promastigote form by a hematophagous diptrous insect, the phlebotomine sand fly, and rapidly become intracellular in their host. The cells currently described as permissive to the *leishmanias* are the cells of the mononuclear phagocyte system. However, a hepatocyte infection test recently demonstrated the permissiveness of this cell type, opening up research perspectives in order to better understand the physiopathology of the infection and to evaluate new therapeutic targets.

1. Materials and Methods

Infection

The *Leishmania major, L. donovani, L. infantum, L. tropica, L. braziliensis* and *L. guyanensis* promastigotes used are strains isolated from patients, identified by the reference isoenzymatic method and cryopreserved in liquid nitrogen. Obtaining an inoculum requires at least 2 successive amplification phases in Novy-McNeal-Nicolle gelose medium with rabbit blood added, then in Schneider medium with 10% of FCS added.

The cells used for the infection were cultured according to the conditions defined in Example 1 (permanent presence of $5.10^{-5}$ M of hydrocortisone hemisuccinate) and maintained for a week at confluence, then for 2 weeks in the same medium with 2% of DMSO added.

These cells are incubated for 18 hours at 37° C. with *leishmania* promastigotes, then washed 3 times with culture medium and maintained in the presence of 2% of DMSO and 5 M hydrocortisone hemisuccinate.

Detection of Intracellular Parasites

The checking and quantification of the infection are carried out by optical microscopy. The cells are recovered after trypsinization of the wells and 2 washings in PBS, cytocentrifuqed for 10 minutes at 9000 rpm, then fixed and stained by May-Grunwald Giemsa stain. The intracellular parasites in amastigote form have cytoplasmic localization, measure 3×6 micrometres and are easily locatable thanks to their structure comprising a bluish cytoplasm, and a violet nucleus and kinetoplast. The number of cells infected and the total number of parasites found are calculated for an average number of 4000 hepatocytes read.

2. Results

Evidence of the Infection

Figure 17:
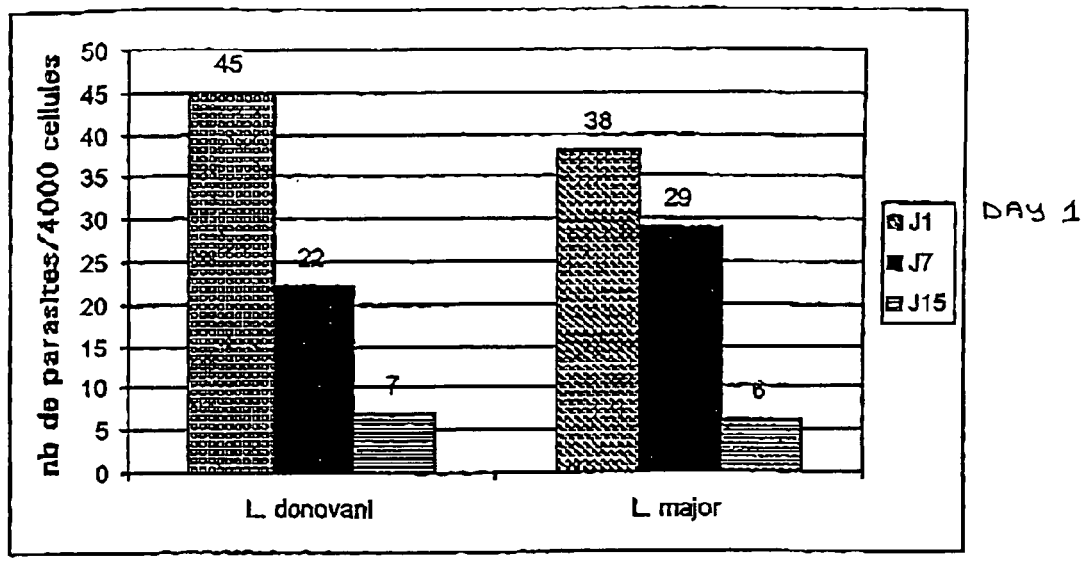

FIG. 17 shows the kinetics of infection observed with an *L. donovani* strain and an *L. major* strain for infection ratios of 25 parasites per cell. The cells can therefore be infected with a hepatotropic strain (*L. donovani*) but also a dermatropic strain (*L. major*). The number of amastigotes of *L. donovani* per 100 cells is comprised between 7 and 45 for 4000 cells read (0.175% to 1.125%), corresponding to a percentage of infected cells comprised between 0.1 to 0.55%. The number of amastigotes of *L. major* is comprised between and 6 and 38 for 4000 cells read (0.15 and 0.725%), corresponding to a percentage of cells infected comprised between 0.1 to 0,375%.

Optimization of the Infection Protocol

Figure 18:
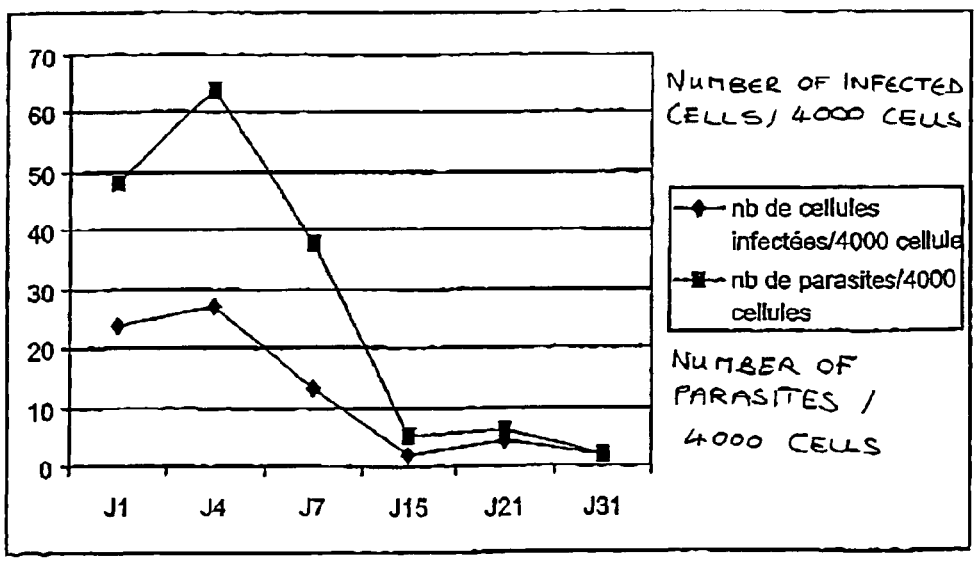

A first experiment studied the "culture duration" effect on the total number of parasites and the number of cells infected. The results of this work carried out with cells infected by *L. major* (infection ratio=25 parasites per cell) are shown in FIG. 18.

Figure 19:
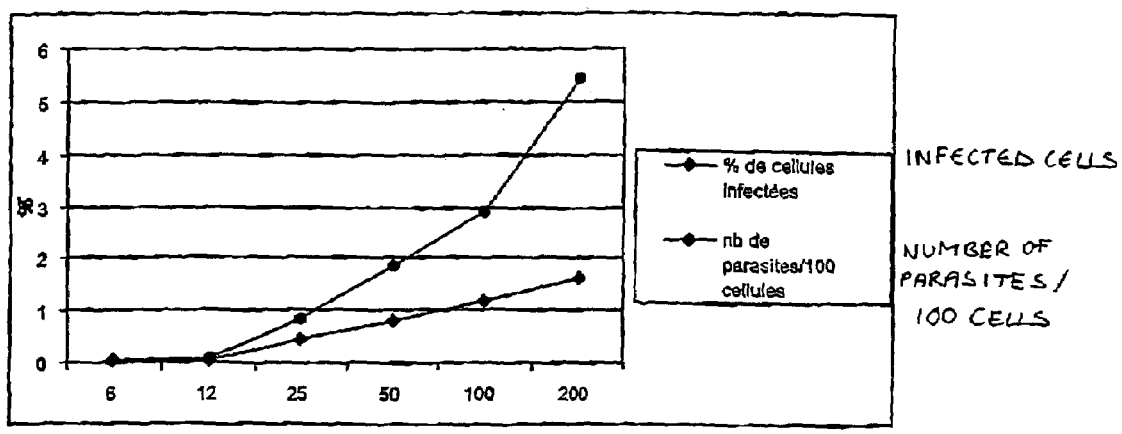

A second experiment aimed at studying the "inoculum" effect on the level of infection of the cells. *L. major* was successively inoculated in the cells with ratios of 6, 12, 25, 50, 100 and 200 parasites per cell. The results of the cultures on Day 7 are shown in FIG. 19 and show that the number of parasites per 100 cells varied from 2 to 218 for 4000 cells read (0.05% to 5.45%), corresponding to a percentage of cells infected ranging from 0.05% to 1.6%.

In total, it appears that the ideal infection ratio by *L. major* is 100 parasites per cell, and the parasite infection quantification is optimum between Day 4 and Day 7.

The invention claimed is:

1. A human hepatoma cell line deposited on 5th Apr. 2001 at the Collection Nationale de Cultures de Microorganismes, Institut pasteur, under No. 1-2652.

2. A method for infecting a human hepatoma cell line with a hepatotropic parasite and/or a virus, the method comprising:
   (1) obtaining the cells of human hepatoma cell line selected for having a hepatocyte-type morphology characteristic of resident liver cells of a human;
   (2) maintaining the selected human hepatoma cell line of (1) in a culture medium comprising at least one cortico-steroid at a non-toxic concentration, and DMSO in a quantity sufficient to induce differentiation; and
   (3) exposing an infectious source comprising a hepatotropic parasite and/or a virus to the human hepatoma cell line of (2) maintained in the culture medium comprising at least one cortico-steroid at a non-toxic concentration to permit infection of the human hepatoma cell line by the parasite and/or the virus,
   wherein the human hepatoma cell line comprises a set of cells derived from a biopsy obtained from a cancerous human liver, the set comprises cells that express a receptor having an affinity for binding a Hepatitis C Virus (HCV) in a native form, and/ or cells that express a receptor having an affinity for binding a Hepatitis B Virus (HBV) in a native form, so that the set of cells are susceptible to infection by HCV and HBV,
   wherein the virus is in a native form and is selected from the group consisting of Hepatitis C Virus (HCV) and or a Hepatitis B Virus (HBV), and
   wherein the hepatotropic parasite is in a native form and is selected from the group consisting of *Leishmania* genus and *Plasmodium falciparum*.

3. The method of claim 2, wherein obtaining the cells of human hepatoma cell line, selected for having a hepatocyte-type morphology characteristic of resident liver cells of a human, comprises:
   (a) providing a biopsy of a solid tumor removed from a hepatocarcinoma patient;
   (b) growing a population of cells derived from the biopsy in a culture medium comprising at least one cortico-steroid at a non-toxic concentration present continuously in the culture medium, during a proliferation phase;
   (c) adding DMSO, in a quantity sufficient to induce differentiation, to the culture medium comprising at least one cortico-steroid exposed to the population of cells so that the culture is continuously exposed to both, a cortico-steroid and DMSO, during a differentiation phase; and
   (d) repeating (b) and (c) as necessary to obtain a subpopulation of cells selected for having a hepatocyte-type morphology characteristic of resident liver cells of a human.

4. A method for maintaining the stability of a human hepatoma cell line, the method comprising:
   continuously exposing the cells of the human hepatoma cell line to a medium comprising at least one cortico-steroid at a non-toxic concentration in order to promote the differentiation of the cells of the human hepatoma cell line so that the differentiated cells develop structural and functional properties characteristic of resident hepatocytes and resident biliary cells of a human liver,
   wherein the human hepatoma cell line comprises a set of cells derived from a biopsy obtained from a cancerous human liver, the set comprises cells that express a receptor having an affinity for binding a Hepatitis C Virus (HCV in a native form, and/ or cells that express a receptor having an affinity for binding a Hepatitis B Virus (HBV) in a native form, so that the set of cells are susceptible to infection by HCV and HBV,
   wherein the medium further comprises sodium butyrate at a concentration sufficient to induce the differentiation of the cells of the human hepatoma cell line into a biliary-type lineage.

5. The method of claim 4, wherein the sodium butyrate is at a concentration of about 2.5 to about 5 mM.

6. The method of claim 4, wherein the sodium butyrate at a concentration of about 3.75 mM.

\* \* \* \* \*

SEQUENCE LISTING

```
<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttgaggttt aggattygtg ctcat                                            25
```

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgagtgtcgt rcagcctcc                                                   19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
accacaaggc ctttcgcrac ccac                                             24
```